(12) United States Patent
Grier et al.

(10) Patent No.: US 11,747,258 B2
(45) Date of Patent: Sep. 5, 2023

(54) HOLOGRAPHIC CHARACTERIZATION OF PROTEIN AGGREGATES

(71) Applicant: NEW YORK UNIVERSITY, New York, NY (US)

(72) Inventors: David G. Grier, New York, NY (US); Michael D. Ward, New York, NY (US); Xiao Zhong, Jersey City, NJ (US); Chen Wang, New York, NY (US); Laura A. Philips, New York, NY (US); David B. Ruffner, New York, NY (US); Fook Chiong Cheong, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 17/826,848

(22) Filed: May 27, 2022

(65) Prior Publication Data

US 2022/0326130 A1 Oct. 13, 2022

Related U.S. Application Data

(63) Continuation of application No. 16/076,265, filed as application No. PCT/US2017/016857 on Feb. 7, 2017, now Pat. No. 11,385,157.

(Continued)

(51) Int. Cl.
*G01N 15/02* (2006.01)
*G01N 15/14* (2006.01)
*G01N 15/00* (2006.01)

(52) U.S. Cl.
CPC ..... *G01N 15/0227* (2013.01); *G01N 15/0211* (2013.01); *G01N 15/147* (2013.01);
(Continued)

(58) Field of Classification Search
CPC ........... G01N 15/0211; G01N 15/0227; G01N 2015/1454; G01N 2015/0053;
(Continued)

(56) References Cited

U.S. PATENT DOCUMENTS 3,069,654 A 12/1962 Hough
3,551,018 A 12/1970 Stetson
(Continued)

FOREIGN PATENT DOCUMENTS

CA 1159674 A1 1/1984
CN 1886684 A 12/2006
(Continued)

OTHER PUBLICATIONS

Allier, et al., "Label-free cell viability assay using lens-free microscopy," SPIE Proceedings 10497, 7 pages (2018).
(Continued)

*Primary Examiner* — Michael P Stafira
(74) *Attorney, Agent, or Firm* — Foley & Lardner LLP

(57) ABSTRACT

Systems and methods for holographic characterization of protein aggregates. Size and refractive index of individual aggregates in a solution can be determined. Information regarding morphology and porosity can be extracted from holographic data.

14 Claims, 13 Drawing Sheets

Related U.S. Application Data

(60) Provisional application No. 62/292,842, filed on Feb. 8, 2016.

(52) U.S. Cl.
CPC ............... *G01N 2015/0038* (2013.01); *G01N 2015/0053* (2013.01); *G01N 2015/0222* (2013.01); *G01N 2015/0233* (2013.01); *G01N 2015/1454* (2013.01)

(58) Field of Classification Search
CPC ... G01N 2015/0233; G01N 2021/4709; G01N 21/49; G01N 2015/0038; G01N 2015/0222; G01N 15/147; G01N 33/483; G01N 15/1434; G01N 21/658; G01N 15/0205; G01N 2015/0277; G01N 2015/0693; G01N 15/1429; G01N 21/47; G01N 21/4795; G01N 15/1463; G01N 2015/0092; G01N 2015/1497; G01N 2021/655; G01N 21/21; G01N 15/14; G01N 2015/0065; G01N 2015/1493; G01N 33/5017; G01N 11/165; G01N 15/1459; G01N 15/1475; G01N 2015/1445; G01N 2021/258; G01N 2021/4714; G01N 2021/7773; G01N 21/359; G01N 21/65; G01N 21/8803; G01N 2201/0616; G01N 2201/068; G01N 2201/12; G01N 33/553; G01N 33/574; G01N 33/587; G01N 33/6875; G01N 1/30; G01N 15/00; G01N 15/088; G01N 15/1468; G01N 15/1484; G01N 2015/003; G01N 2015/03; G01N 2021/4707; G01N 2021/4792; G01N 21/3563; G01N 21/3577; G01N 21/4133; G01N 21/453; G01N 2201/0612; G01N 2201/062; G01N 2201/067; G01N 2201/129; G01N 2223/423; G01N 2223/6126; G01N 23/046; G01N 2800/52; G01N 33/4833; G01N 33/49; G01N 33/5091; G01N 21/554

See application file for complete search history.

(56) References Cited

U.S. PATENT DOCUMENTS

| | | | |
|---|---|---|---|
| 4,532,422 A | 7/1985 | Nomura et al. |
| 4,540,285 A | 9/1985 | Amer |
| 4,627,729 A | 12/1986 | Breuckmann et al. |
| 4,740,079 A | 4/1988 | Koizumi et al. |
| 4,986,659 A | 1/1991 | Bachalo |
| 4,998,788 A | 3/1991 | Osakabe et al. |
| 5,095,207 A | 3/1992 | Tong |
| 5,146,086 A | 9/1992 | De et al. |
| 5,373,727 A | 12/1994 | Heller et al. |
| 5,796,498 A | 8/1998 | French |
| 5,880,841 A | 3/1999 | Marron et al. |
| 5,939,716 A | 8/1999 | Neal |
| 6,055,106 A | 4/2000 | Grier et al. |
| 6,097,488 A | 8/2000 | Grek et al. |
| 6,214,560 B1 | 4/2001 | Yguerabide et al. |
| 6,281,994 B1 | 8/2001 | Horikoshi et al. |
| 6,424,677 B1 | 7/2002 | Moeller et al. |
| 6,480,285 B1 | 11/2002 | Hill |
| 6,507,839 B1 | 1/2003 | Ponte |
| 6,519,033 B1 | 2/2003 | Quist et al. |
| 6,624,940 B1 | 9/2003 | Grier et al. |
| 6,680,798 B2 | 1/2004 | Kreuzer |
| 6,710,874 B2 | 3/2004 | Mavliev |
| 6,797,942 B2 | 9/2004 | Grier et al. |
| 6,815,664 B2 | 11/2004 | Wang et al. |
| 6,850,363 B1 | 2/2005 | Wendenburg et al. |
| 6,858,833 B2 | 2/2005 | Curtis et al. |
| 6,977,767 B2 * | 12/2005 | Sarychev ............... G02F 1/3515 359/290 |
| 6,995,351 B2 | 2/2006 | Curtis et al. |
| 7,001,721 B1 | 2/2006 | Whitcombe et al. |
| 7,109,473 B2 | 9/2006 | Grier et al. |
| 7,133,203 B2 | 11/2006 | Grier et al. |
| 7,161,140 B2 | 1/2007 | Grier et al. |
| 7,218,112 B2 | 5/2007 | Ladebeck et al. |
| 7,232,989 B2 | 6/2007 | Grier et al. |
| 7,233,423 B2 | 6/2007 | Grier |
| 7,248,282 B2 | 7/2007 | Maddison |
| 7,276,170 B2 | 10/2007 | Oakey et al. |
| 7,324,282 B2 | 1/2008 | Grier et al. |
| 7,338,168 B2 | 3/2008 | Cartlidge et al. |
| 7,351,953 B2 | 4/2008 | Grier et al. |
| 7,473,890 B2 | 1/2009 | Grier et al. |
| 7,482,577 B2 | 1/2009 | Gruber et al. |
| 7,491,928 B2 | 2/2009 | Roichman et al. |
| 7,515,953 B2 | 4/2009 | Madar et al. |
| 7,532,327 B2 | 5/2009 | Bloom et al. |
| 7,835,051 B2 | 11/2010 | Roichman et al. |
| 7,839,551 B2 | 11/2010 | Lee et al. |
| 7,869,011 B2 * | 1/2011 | Christensen ......... G01N 21/645 356/72 |
| 7,875,845 B2 | 1/2011 | Plewa et al. |
| 7,908,300 B2 | 3/2011 | Stluka et al. |
| 8,059,321 B2 | 11/2011 | Roichman et al. |
| 8,119,988 B2 | 2/2012 | Daido et al. |
| 8,128,242 B2 | 3/2012 | Grier et al. |
| 8,299,789 B2 | 10/2012 | Heid et al. |
| 8,331,019 B2 | 12/2012 | Cheong et al. |
| 8,405,395 B2 | 3/2013 | Setsompop et al. |
| 8,431,884 B2 | 4/2013 | Grier |
| 8,680,861 B1 | 3/2014 | Morrone |
| 8,766,169 B2 | 7/2014 | Grier et al. |
| 8,791,053 B2 * | 7/2014 | Christensen ......... B01J 19/0046 506/13 |
| 8,791,985 B2 | 7/2014 | Grier et al. |
| 9,176,152 B2 | 11/2015 | Knutson et al. |
| 9,810,894 B2 * | 11/2017 | Grier ..................... G02B 21/361 |
| 11,385,157 B2 * | 7/2022 | Grier ..................... G01N 15/147 |
| 2002/0069242 A1 | 6/2002 | Berns |
| 2003/0007894 A1 | 1/2003 | Wang et al. |
| 2003/0021016 A1 | 1/2003 | Grier |
| 2003/0021382 A1 | 1/2003 | Iwanczyk et al. |
| 2003/0047676 A1 | 3/2003 | Grier et al. |
| 2003/0089117 A1 | 5/2003 | Mao et al. |
| 2003/0132373 A1 | 7/2003 | Curtis et al. |
| 2004/0004716 A1 | 1/2004 | Mavliev |
| 2004/0004717 A1 | 1/2004 | Reed |
| 2004/0058455 A1 | 3/2004 | Grier et al. |
| 2004/0072372 A1 | 4/2004 | Seul et al. |
| 2004/0156098 A1 | 8/2004 | Dubois et al. |
| 2004/0180363 A1 | 9/2004 | Gruber et al. |
| 2004/0207922 A1 | 10/2004 | Grier et al. |
| 2005/0017161 A1 | 1/2005 | Grier et al. |
| 2005/0059846 A1 | 3/2005 | Kohda et al. |
| 2005/0141757 A1 | 6/2005 | Ayache et al. |
| 2005/0173622 A1 | 8/2005 | Curtis et al. |
| 2005/0176134 A1 | 8/2005 | Grier et al. |
| 2006/0003252 A1 | 1/2006 | Hirayama et al. |
| 2006/0029634 A1 | 2/2006 | Berg et al. |
| 2006/0127369 A1 | 6/2006 | Christensen et al. |
| 2006/0131494 A1 | 6/2006 | Grier et al. |
| 2006/0163463 A1 | 7/2006 | Grier |
| 2007/0023622 A1 | 2/2007 | Grier et al. |
| 2007/0070303 A1 | 3/2007 | Yonekubo |
| 2007/0091442 A1 | 4/2007 | Macdonald et al. |
| 2007/0177774 A1 | 8/2007 | Kuo |
| 2007/0242269 A1 | 10/2007 | Trainer |
| 2008/0037004 A1 | 2/2008 | Shamir et al. |
| 2008/0094675 A1 | 4/2008 | Roichman et al. |
| 2008/0137161 A1 | 6/2008 | Roichman et al. |
| 2008/0150532 A1 | 6/2008 | Slavin et al. |
| 2008/0285099 A1 | 11/2008 | Knutson et al. |
| 2009/0027747 A1 | 1/2009 | Lee et al. |

(56) References Cited

U.S. PATENT DOCUMENTS

| | | |
|---|---|---|
| 2009/0059008 A1 | 3/2009 | Ishii |
| 2009/0073563 A1 | 3/2009 | Betzig |
| 2009/0079981 A1* | 3/2009 | Holve .............. G01N 15/0205 356/336 |
| 2009/0128825 A1 | 5/2009 | Akcakir |
| 2009/0132074 A1 | 5/2009 | Yamada |
| 2009/0135432 A1 | 5/2009 | Betzig |
| 2009/0170186 A1 | 7/2009 | Wu et al. |
| 2010/0055031 A1 | 3/2010 | Ahn |
| 2010/0090694 A1 | 4/2010 | Heid et al. |
| 2010/0150408 A1 | 6/2010 | Ishikawa |
| 2010/0172591 A1 | 7/2010 | Ishikawa |
| 2010/0241357 A1 | 9/2010 | Chan et al. |
| 2010/0253986 A1 | 10/2010 | Awatsuji et al. |
| 2010/0259263 A1 | 10/2010 | Holland et al. |
| 2011/0043607 A1 | 2/2011 | Grier et al. |
| 2011/0071764 A1 | 3/2011 | Prather et al. |
| 2011/0126914 A1 | 6/2011 | Hartman et al. |
| 2011/0130348 A1 | 6/2011 | Ting et al. |
| 2011/0157599 A1 | 6/2011 | Weaver et al. |
| 2011/0225196 A1 | 9/2011 | Haseyama |
| 2011/0292363 A1 | 12/2011 | Ivey et al. |
| 2012/0135535 A1 | 5/2012 | Grier et al. |
| 2012/0177543 A1 | 7/2012 | Battrell et al. |
| 2012/0183947 A1 | 7/2012 | Mueth et al. |
| 2012/0235678 A1 | 9/2012 | Seiberlich et al. |
| 2012/0256626 A1 | 10/2012 | Adalsteinsson et al. |
| 2012/0273664 A1 | 11/2012 | Grier et al. |
| 2013/0038326 A1 | 2/2013 | Amadon et al. |
| 2013/0271135 A1 | 10/2013 | Ozen et al. |
| 2013/0278743 A1 | 10/2013 | Cheong et al. |
| 2013/0308135 A1 | 11/2013 | Dubois et al. |
| 2014/0148547 A1 | 5/2014 | Ishida et al. |
| 2014/0170735 A1 | 6/2014 | Holmes |
| 2014/0177932 A1 | 6/2014 | Milne et al. |
| 2014/0253126 A1 | 9/2014 | Habara et al. |
| 2014/0313510 A1 | 10/2014 | Schmidt et al. |
| 2014/0333935 A1 | 11/2014 | Grier et al. |
| 2015/0002150 A1 | 1/2015 | Weissler et al. |
| 2015/0062587 A1 | 3/2015 | Shpaisman |
| 2015/0300963 A1 | 10/2015 | Haidekker et al. |
| 2015/0301141 A1 | 10/2015 | Griswold et al. |
| 2015/0346300 A1 | 12/2015 | Setsompop et al. |
| 2017/0209864 A1 | 7/2017 | Grisham et al. |
| 2018/0252628 A1 | 9/2018 | Ruffner et al. |
| 2021/0123848 A1 | 4/2021 | Grier et al. |
| 2021/0199552 A1 | 7/2021 | Van Oostrum et al. |

FOREIGN PATENT DOCUMENTS

| | | | |
|---|---|---|---|
| CN | 103238120 A * | 8/2013 | ............ G01B 9/021 |
| EP | 0 354 37 A1 | 9/1981 | |
| EP | 0 278 714 A2 | 8/1988 | |
| EP | 1 855 081 A1 | 11/2007 | |
| EP | 1 865 430 A2 | 12/2007 | |
| GB | 2 408 587 A | 6/2005 | |
| JP | 55-096976 A | 7/1980 | |
| JP | 03-251388 A | 11/1991 | |
| JP | 03-251888 A | 11/1991 | |
| JP | 2000-225302 A | 8/2000 | |
| JP | 2001-034148 A | 2/2001 | |
| JP | 2004-517742 A | 6/2004 | |
| JP | 2005-512127 A | 4/2005 | |
| JP | 2007-279475 A | 10/2007 | |
| JP | 2011-502256 A | 1/2011 | |
| JP | 2011-525967 A | 9/2011 | |
| JP | 2012-515351 A1 | 7/2012 | |
| JP | 2014-503794 A | 2/2014 | |
| WO | WO-0115288 A1 * | 3/2001 | ............ B82Y 10/00 |
| WO | WO-03/048868 A1 | 6/2003 | |
| WO | WO-2005/027031 A2 | 3/2005 | |
| WO | WO-2005/114151 A1 | 12/2005 | |
| WO | WO-2006/034129 A2 | 3/2006 | |
| WO | WO-2008/092107 A1 | 7/2008 | |
| WO | WO-2008/127410 A2 | 10/2008 | |
| WO | WO-2008/142560 A2 | 11/2008 | |
| WO | WO-2009/059008 A1 | 5/2009 | |
| WO | WO-2010/101671 A1 | 9/2010 | |
| WO | WO-2012/061752 A2 | 5/2012 | |
| WO | WO-2013/080164 A1 | 6/2013 | |
| WO | WO-2013/126554 A1 | 8/2013 | |
| WO | WO-2015/073894 A2 | 5/2015 | |
| WO | WO-2015/200512 A1 | 12/2015 | |
| WO | WO-2015200512 A1 * | 12/2015 | ......... G01N 15/0211 |
| WO | WO-2021/249692 A1 | 12/2021 | |
| WO | WO-2021/249693 A1 | 12/2021 | |

OTHER PUBLICATIONS

Alm, et al., "Cells and Holograms—Holograms and Digital Holographic Microscopy as a Tool to Study the Morphology of Living Cells," Holography—Basic Principles and Contemporary Applications, pp. 335-351 (2013).

Arrizon, et al., "Accurate encoding of arbitrary complex fields with amplitude-only liquid crystal spatial light modulators," Optics Express 13(20), pp. 7913-7927 (2005).

Botstein & Fink, "Yeast: An Experimental Organism for 21st Century Biology," Genetics 189(3), pp. 695-704 (2011).

Chan, et al., "Morphological observation and analysis using automated image cytometry for the comparison of trypan blue and fluorescence-based viability detection method," Cytotechnology 67, pp. 461-473 (2014).

Chan, et al., "Observation and quantification of the morphological effect of trypan blue rupturing dead or dying cells," PLoS ONE 15(1):e0227950, 17 pages (2020).

Cheong, et al., "Rapid, High-Throughput Tracking of Bacterial Motility in 3D via Phase-Contrast Holographic Video Microscopy," Biophysical Journal 108(5), pp. 1248-1256 (2015).

Cuche, et al., "Simultaneous amplitude-contrast and quantitative phase-contrast microscopy by numerical reconstruction of Fresnel off-axis holograms," Applied Optics 38(34), pp. 6994-7001 (1999).

Davis, et al., "Encoding amplitude and phase information onto a binary phase-only spatial light modulator," Applied Optics 42(11), pp. 2003-2008 (2003).

Davis, et al., "Encoding amplitude information onto phase-only filters," Applied Optics 38(23), pp. 5004-5013 (1999).

Duina, et al., "Budding Yeast for Budding Geneticists: A Primer on the *Saccharomyces cerevisiae* Model System," Genetics 197(1), pp. 33-48 (2014).

Feizi, et al., "Lensfree On-chip Microscopy Achieves Accurate Measurement of Yeast Cell Viability and Concentration Using Machine Learning," Conference on Lasers and Electro-Optics, ATh4B.4, 2 pages (2017).

Feizi, et al., "Rapid, portable and cost-effective yeast cell viability and concentration analysis using lensfree on-chip microscopy and machine learning," Lab on a Chip 16(22), pp. 4350-4358 (2016).

Ferreira, et al., "Tackling Cancer with Yeast-Based Technologies," Trends in Biotechnology 37(6), pp. 592-603 (2019).

Fleet, "Yeasts in foods and beverages: impact on product quality and safety," Current Opinion in Biotechnology 18(2), pp. 170-175 (2007).

Gabor, "A New Microscopic Principle," Nature 161, pp. 777-778 (1948).

Gibson, et al., "Yeast responses to stresses associated with industrial brewery handling," FEMS Microbiology REviews 31(5), pp. 535-569 (2007).

Gomes, et al., "Comparison of Yeasts as Hosts for Recombinant Protein Production," Microorganisms 6(2):38, 23 pages (2018).

Gorbenko, et al., "Quantification of changes in cellular morphology during cell necrosis obtained from 3D refractive index distributions," Journal of Physics: Conference Series 1236:012015, 6 pages (2019).

Guaragnella, et al., "The expanding role of yeast in cancer research and diagnosis: insights into the function of the oncosuppressors p53 and BRCA1/2," FEMS Yeast Research 14(1), pp. 2-16 (2014).

(56) References Cited

OTHER PUBLICATIONS

Huang, et al., "Efficient protein production by yeast requires global tuning of metabolism," Nature Communications 8:1131, 12 pages (2017).
Huang, et al., "Optical tweezers as sub-pico-newton force transducers," Optics Communications 195(1-4), pp. 41-48 (2001).
Kasimbeg, et al., "Holographic Characterization of Protein Aggregates in the Presence of Silicone Oil and Surfactants," Journal of Pharmaceutical Sciences 108(1), pp. 155-161 (2019).
Kim, et al., "Yeast synthetic biology for the production of recombinant therapeutic proteins," FEMS Yeast Research 15(1), pp. 1-16 (2015).
Kwolek-Mirkek & Zadrag-Tecza, "Comparison of methods used for assessing the viability and vitality of yeast cells," FEMS Yeast Research 14(7), pp. 1068-1079 (2014).
Lodolo, et al., "The yeast *Saccharomyces cerevisiae*-the main character in beer brewing," FEMS Yeast Research 8(7), pp. 1018-1036 (2008).
Maicas, "The Role of Yeasts in Fermentation Processes," Microorganisms 8(8): 1142, 8 pages (2020).
Markel, et al., "Introduction to the Maxwell Garnett approximation: tutorial," Journal of the Optical Society of America A 33(7), pp. 1244-1256 (2016).
Mascotti, et al., "HPC viability measurement: trypan blue versus acridine orange and propidium iodide," Transfusion 40(6), pp. 693-696 (2000).
Merner, et al., "Cell viability assessment by flow cytometry using yeast as cell model," Sensors & Actuators B: Chemical 154(2), pp. 160-163 (2011).
Midtvedt, et al., "Label-free spatio-temporal monitoring of cytosolic mass, osmolarity, and volume in living cells," Nature Communications 10:340, 9 pages (2019).
Moh, et al., "Multiple optical line traps using a single phase-only rectangular ridge," Applied Physics B 80(8), pp. 973-976 (2005).
Neuman & Block, "Optical trapping," Review of Scientific Instruments 75(9), pp. 2787-2809 (2004).
Odete, et al., "The role of the medium in the effective-sphere interpretation of holographic particle characterization data," Soft Matter 16(4), pp. 891-898 (2019).
Odumeru, et al., "Effects of heat shock and ethanol stress on the viability of a *Saccharomyces uvarum* (carlsbergensis) brewing yeast strain during fermentation of high gravity wort," Journal of Industrial Microbiology 10(2), pp. 111-116 (1992).
Ovryn & Izen, "Imaging of transparent spheres through a planar interface using a high-numerical-aperture optical microscope," Journal of the Optical Society of America A 17(7), pp. 1202-1213 (2000).
Parapouli, et al., "*Saccharomyces cerevisiae* and its industrial applications," AIMS Microbiology 6(1), pp. 1-31 (2020).
Philips, et al., "Holographic characterization of contaminants in water: Differentiation of suspended particles in heterogeneous dispersions," Water Research 122, pp. 431-439 (2017).
Pralle, et al., "Three-dimensional high-resolution particle tracking for optical tweezers by forward scattered light," Microscopy Research & Technique 44(5), pp. 378-386 (1999).
Pratt, et al., "The Effects of Osmotic Pressure and Ethanol on Yeast Viability and Morphology," Journal of the Institute of Brewing 109(3), pp. 218-228 (2003).
Pray, "L. H. Hartwell's Yeast: A Model Organism for Studying Somatic Mutations and Cancer," Nature Education 1(1), 3 pages (2008).
Rommel, et al., "Contrast-enhanced digital holographic imaging of cellular structures by manipulating the intracellular refractive index," Journal of Biomedical Optics 15(4):041509, 10 pages (2010).
Schnars & Juptner, "Direct recording of holograms by a CCD target and numerical reconstruction," Applied Optics 33(2), pp. 179-181 (1994).
Seo, et al., "Lensfree holographic imaging for on-chip cytometry and diagnostics," Lab on a Chip 9(6), pp. 777-787 (2009).
Tennant, "Evaluation of the Trypan Blue Technique for Determination of Cell Viability," Transplantation 2(6), pp. 685-694 (1964).
Winters, et al., "Quantitative Differentiation of Protein Aggregates From Other Subvisible Particles in Viscous Mixtures Through Holographic Characterization," Journal of Pharmaceutical Sciences 109(8), pp. 2405-2412 (2020).
Xu, et al., "Digital in-line holograhy of microspheres," Applied Optics 41(25), pp. 5367-5375 (2002).
Zhang, et al., "Reconstruction algorithm for high-numerical-aperture holograms with diffraction-limited resolution," Optics Letters 31(11), pp. 1633-1635 (2006).
Crocker & Grier, "Methods of Digital Video Microscopy for Colloidal Studies," Methods of Digital Video Microscopy for Colloidal Studies 179(1), pp. 298-310 (1996).
Daimon & Masumura, "Measurement of the refractive index of distilled water from the near-infrared region to the ultraviolet region," Applied Optics 46(18), pp. 3811-3820 (2007).
Dufresne, et al., "Brownian dynamics of a sphere between parallel walls," Europhysics Letters 53(2), pp. 264-270 (2001).
Krishnatreya, et al., "Measuring Boltzmann's constant through holographic video microscopy of a single colloidal sphere," American Journal of Physics 82(1):23, 10 pages (2014).
Lin, et al., "Direct measurements of constrained Brownian motion of an isolated sphere between two walls," Physical Review E 62(3), pp. 3909-3919 (2000).
Lobry & Ostrowsky, "Diffusion of Brownian particles trapped between two walls: Theory and dynamic-light-scattering measurements," Physical Review B 53(18), pp. 12050-12056 (1996).
Plumere, et al., "Stober silica particles as basis for redox modifications: Particle shape, size, polydispersity, and porosity," Journal of Colloid and Interface Science 368(1), pp. 208-219 (2012).
Power & De Power, "Second-Kind Integral Equation Formulation for the Slow Motion of a Particle of Arbitrary Shape Near a Plane Wall in a Viscous Fluid," SIAM Journal on Applied Mathematics 53(1), pp. 60-70 (1993).
Sohn, "Refractive Index of Porous Silicon," Handbook of Porous Silicon, pp. 231-243 (2014).
Van Oostrum, "Using Light Scattering to Track, Characterize and Manipulate Colloids," Utrecht University Repository, PhD Thesis, 321 pages (2011).
Xue, et al., "Diffusion, dispersion, and settling of hard spheres," Physical Review Letters 69(11), pp. 1715-1718 (1992).
Meakin, "Fractal Aggregates", Advances in Colloid and Interface Science, 1988, 28:249-331.
International Search Report and Written Opinion in PCT/US2017/016857, dated Jun. 9, 2017, 13 pages.
"Immunogenicity Assessment for Therapeutic Protein Products," Food and Drug Administration, 39 pages (2014).
Aspnes, "Local-field effects and effective-medium theory: A microscopic perspective," American Journal of Physics 50(8), pp. 704-709 (1982).
Atherton & Kerbyson, "Size invariant circle detection," Image and Vision Computing 17(11), pp. 795-803 (1999).
Ball, et al., "Complexation Mechanism of Bovine Serum Albumin and Poly(allylamine hydrochloride)," The Journal of Physical Chemistry B 106(9), pp. 2357-2364 (2002).
Ballard, "Generalizing the Hough transform to detect arbitrary shapes," Pattern Recognition 13(2), pp. 111-122 (1981).
Basim & Moudgil, "Effect of Soft Agglomerates on CMP Slurry Performance," Journal of Colloid and Interface Science 256(1), pp. 137-142 (2002).
Basim, et al., "Effect of Particle Size of Chemical Mechanical Polishing Slurries for Enhanced Polishing with Minimal Defects," Journal of the Electrochemical Society 147(9), pp. 3523-3528 (2000).
Ben-Eliezer, et al., "A New Model-Based Technique for Accurate Reconstruction of T2 Relaxation Maps from Fast Spin-Echo Data," Proceedings of the International Society for Magnetic Resonance in Medicine 21, p. 2453 (2013).
Bishop, "Inverse problems," Neural Networks for Pattern Recognition, p. 207 (1995).

(56) References Cited

OTHER PUBLICATIONS

Boas, et al., "Scattering of diffuse photon density waves by spherical inhomogeneities within turbid media: analytic solution and applications," Proceedings of the National Academy of Sciences 91(11), pp. 4887-4891 (1994).
Bolognesi, et al., "Digital holographic tracking of microprobes for multipoint viscosity measurements," Optics Express 19(20), p. 19245-19254 (2011).
Bourquard, et al., "A practical inverse-problem approach to digital holographic reconstruction," Optics Express 23(3), pp. 3417-3433 (2013).
Carpenter, et al., "Overlooking subvisible particles in therapeutic protein products: Gaps that may compromise product quality," Journal of Pharmaceutical Sciences 98(4), pp. 1201-1205 (2009).
Chang & Lin, "LIBSVM: A library for support vector machines," ACM Transactions on Intelligent Systems and Technology 2(3), 27, 27 pages (2011).
Chang & Lin, "Training v-Support Vector Regression: Theory and Algorithms," Neural Computation 14(8), pp. 1959-1977 (2002).
Chen, et al., "Magnetic resonance fingerprinting (MRF) for rapid quantitative abdominal imaging," Proceedings of the International Society for Magnetic Resonance in Medicine 22, p. 0561 (2014).
Cheong & Grier, "Rotational and translational diffusion of copper oxide nanorods measured with holographic video microscopy," Optics Express 18(7), pp. 6555-6562 (2010).
Cheong, et al., "Flow visualization and flow cytometry with holographic video microscopy," Optics Express 17(15), pp. 13071-13079 (2009).
Cheong, et al., "Holographic characterization of individual colloidal spheres' porosities," Soft Matter 7(15), pp. 6816-6819 (2011).
Cheong, et al., "Holographic microrheology of polysaccharides from Streptococcus mutans biofilms," Rheologica Acta 48(1), pp. 109-115 (2009).
Cheong, et al., "Strategies for three-dimensional particle tracking with holographic video microscopy," Optics Express 18(13), pp. 13563-13573 (2010).
Cheong, et al., "Technical note: Characterizing individual milk fat globules with holographic video microscopy," Journal of Dairy Science 92(1), pp. 95-99 (2009).
Chia, et al., "A Review of Analytical Techniques for Identifying Contaminants in the Semiconductor Industry," Journal of the IEST 45(1), pp. 37-44 (2002).
Cloos, et al., "Plug and Play Parallel Transmission at 7 and 9.4 Tesla Based on Principles from MR Fingerprinting," Proceedings of the International Society for Magnetic Resonance in Medicine 22, p. 0542 (2014).
Colomb, et al., "Polarization microscopy by use of digital holography: application to optical-fiber birefringence measurements," Applied Optics 44(21), pp. 4461-4469 (2005).
Costantino, et al., "Moisture-Induced Aggregation of Lyophilized Insulin," 11(1), pp. 21-29 (1994).
Crocker & Grier, "Methods of Digital Video Microscopy for Colloidal Studies," Journal of Colloid and Interface Science 179(1), pp. 298-310 (1996).
Demeule, et al., "Characterization of Particles in Protein Solutions: Reaching the Limits of Current Technologies," The AAPS Journal 12(4), pp. 708-715 (2010).
Den Engelsman, et al., "Strategies for the Assessment of Protein Aggregates in Pharmaceutical Biotech Product Development," Pharmaceutical Research 28(4), pp. 920-933 (2011).
Denis, et al., "Direct Extraction of the Mean Particle Size from a Digital Hologram," Applied Optics 45(5), pp. 944-952 (2006).
Dixon, et al., "Holographic deconvolution microscopy for high-resolution particle tracking," Optics Express 19(17), pp. 16410-16417 (2011).
Dixon, et al., "Holographic particle-streak velocimetry," Optics Express 19(5), pp. 4393-4398 (2011).
Doneva, et al., "Compressed Sensing Reconstruction for Magnetic Resonance Parameter Mapping," Magnetic Resonance in Medicine 64, pp. 1114-1120 (2020).
Dumm, "Characterization of low-level, oversize particles in abrasive powders," KONA Powder and Particle Journal 23, pp. 129-138 (2005).
Egorov, "Systematika, printsipy raboty i oblasty primeneniya datchikov (Systematics, the principle of operation and sensor applications)", Zhurnal radioelectoniki (Journal of Radio Electronics) 3, 22 pages (English abstract) (2009).
Examination Report for European Patent App. No. 08844591.1 dated Jan. 23, 2012, 6 pages.
Extended European Search Report for European Patent App. No. 08844591.1 dated Nov. 5, 2011, 7 pages.
Extended European Search Report for European Patent App. No. 15152531.8, dated Mar. 20, 2015, 4 pages.
Extended European Search Report for European Patent App. No. 16169799.0, dated Aug. 18, 2016, 7 pages.
Extended European Search Report for European Patent App. No. 17750639.1 dated Jan. 16, 2020, 13 pages.
Feder, et al.,. "Scaling Behavior and Cluster Fractal Dimension Determined by Light Scattering from Aggregating Proteins," Physical Review Letters 53(15), pp. 1403-1406 (1984).
Fifth Office Action for Chinese Patent App. No. 201080009712.X, dated Mar. 11, 2015, 17 pages (with translation).
Filipe, et al., "Critical Evaluation of Nanoparticle Tracking Analysis (NTA) by NanoSight for the Measurement of Nanoparticles and Protein Aggregates," Pharmaceutical Research 27(5), pp. 796-810 (2010).
Fung & Manoharan, "Holographic measurements of anisotropic three-dimensional diffusion of colloidal clusters," Physical Review E 88(2), 020302(R), 9 pages (2013).
Fung, et al., "Imaging multiple colloidal particles by fitting electromagnetic scattering solutions to digital holograms," Journal of Quantitative Spectroscopy and Radiative Transfer 113(18), pp. 2482-2489 (2012).
Fung, et al., "Measuring translational, rotational, and vibrational dynamics in colloids with digital holographic microscopy," Optics Express 19(9), pp. 8051-8065 (2011).
Goller, et al., "Inorganic "silicone oil" microgels," Colloids and Surfaces A: Physicochemical and Engineering Aspects 123-124, pp. 183-193 (1997).
Goodman, "Statistical Properties of Laser Speckle Patterns," Laser Speckle and Related Phenomena, pp. 9-75 (2007).
Graesslin, et al., "Fully Integrated Whole Body 3T MRI System for Parallel RF Transmission", Proceedings of the International Society for Magnetic Resonance in Medicine 15, p. 1007 (2007).
Graesslin, et al., "Whole Body 3T MRI System with Eight Parallel RF Transmission Channels," Proceedings of the International Society for Magnetic Resonance in Medicine 14, p. 129 (2006).
Grier, "A revolution in optical manipulation," Nature 424, pp. 810-816 (2003).
Grier, "Downloadable holographic microscopy software written in IDL, the Interactive Data Language," retrieved from http://physics.nyu.edu/grierlab/software.html, 3 pages (2014).
Hagiwara, et al., "Fractal Analysis of Aggregates Formed by Heating Dilute BSA Solutions Using Light Scattering Methods," Bioscience, Biotechnology, and Biochemistry 60(11), pp. 1757-1763 (1996).
Haist, et al., "Using Graphics Boards to Compute Holograms," Computing in Science & Engineering 8, pp. 8-13 (2006).
Hannel, et al., "Holographic characterization of imperfect colloidal spheres," Applied Physics Letters 107(14), 141905, 4 pages (2015).
Hillman, et al., "Microscopic particle discrimination using spatially-resolved Fourier-holographic light scattering angular spectroscopy," Optics Express 14(23), pp. 11088-11102 (2006).
Hogg, "Issues in Particle Size Analysis," KONA Powder and Particle Journal 26, pp. 81-93 (2008).
Hollitt, "A convolution approach to the circle Hough transform for arbitrary radius," Machine Vision and Applications 24(4), pp. 683-694 (2013).
Holm, et al., "Aggregation and fibrillation of bovine serum albumin," Biochimica et Biophysica Acta (BBA) - Proteins and Proteomics 1774(9), pp. 1128-1138 (2007).

(56) References Cited

OTHER PUBLICATIONS

HUKKANEN & BRAATZ, "Measurement of particle size distribution in suspension polymerization using in situ laser backscattering," Sensors and Actuators B: Chemical 96(1-2), pp. 451-459 (2003).
International Search Report & Written Opinion for PCT/US2008/081794 dated Feb. 12, 2009, 5 pages.
International Search Report & Written Opinion for PCT/US2010/021045 dated Apr. 30, 2010, 6 pages.
International Search Report & Written Opinion for PCT/US2012/051542 dated Nov. 22, 2012, 6 pages.
International Search Report and Written Opinion for PCT/US2015/015666, dated Jan. 7, 2016, 11 pages.
International Search Report and Written Opinion for PCT/US2015/037472, dated Sep. 23, 2015, 9 pages.
International Search Report and Written Opinion for PCT/US2015/055154, dated Jan. 7, 2016, 11 pages.
International Search Report and Written Opinion for PCT/US2015/060183, dated Feb. 2, 2016, 9 pages.
International Search Report and Written Opinion for PCT/US2016/051946 dated Nov. 28, 2016, 7 pages.
Ishimaru, "Diffusion of light in turbid material," Applied Optics 28(12), pp. 2210-2215 (1989).
Jones, et al., "Silicone oil induced aggregation of proteins," Journal of Pharmaceutical Sciences 94(4), pp. 918-927 (2005).
Kao, et al., "Tracking of Single Fluorescent Particles in Three Dimensions: Use of Cylindrical Optics to Encode Particle Position," Biophysical Journal 67(3), pp. 1291-1300 (1994).
Katscher, et al., "Parallel RFtransmission in Mri", Nmr in Biomedicine 19(3), pp. 393-400 (2006).
Katscher, et al., "RF Encoding Using a Multielement Parallel Transmit System," Magnetic Resonance in Medicine 63(6), pp. 1463-1470 (2010).
Knoll, et al., "Simultaneous MR-PET Reconstruction Using Multi Sensor Compressed Sensing and Joint Sparsity," Proceedings of the International Society for Magnetic Resonance in Medicine 22, p. 0082 (2014).
Kolomenkin, et al., "Geometric Voting Algorithm for Star Trackers," IEEE Transactions on Aerospace and Electronic Systems 44(2), 441-456 (2008).
Kosters, et al., "EMRECON: An Expectation Maximization Based Image Reconstruction Framework for Emission Tomography Data", 2011 IEEE Nuclear Science Symposium Conference Record, pp. 4365-4368 (2011).
Krishnatreya, et al., "Fast feature identification for holographic tracking: the orientation alignment transform," Optics Express 22(11), pp. 12773-12778 (2014).
Krishnatreya, et al., "Measuring Boltzmann's constant through holographic video microscopy of a single colloidal sphere," American Journal of Physics 82(23), pp. 23-31 (2014).
Lee, et al., "Characterizing and tracking single colloidal particles with video holographic microscopy," Optics Express 15(26), pp. 18275-18282 (2007).
Lee, et al., "Holographic microscopy of holographically trapped three-dimensional structures", Optics Express 15(4), pp. 1505-1512 (2007).
Lee, et al., "Statistics of speckle propagation through the turbulent atmosphere," Journal of the Optical Society of America 66(11), pp. 1164-1172 (1976).
Li, et al., "Understanding Stober Silica's Pore Characteristics Measured by Gas Adsorption," Langmuir 31 (2), pp. 824-832 (2015).
Ma, et al., "Magnetic resonance fingerprinting," Nature 495, pp. 187-193 (2013).
Malitson, "Interspecimen Comparison of the Refractive Index of Fused Silica," Journal of the Optical Society of America 55(10), pp. 1205-1209 (1965).
Maret & Wolf, "Multiple light scattering from disordered media. The effect of brownian motion of scatterers," Zeitschrift fur Physik B Condensed Matter 65(4), pp. 409-413 (1987).
Maschke, et al., "Micronization of Insulin by High Pressure Homogenization," Pharmaceutical Research 23(9), pp. 2220-2229 (2006).
Moreno, et al., "Particle positioning from charge-coupled device images by the generalized Lorenz-Mie theory and comparison with experiment," Applied Optics 39(28), pp. 5117-5124 (2000).
Moyses, et al., "Robustness of Lorenz-Mie microscopy against defects in illumination," Optics Express 21(5), pp. 5968-5973 (2013).
Mueller, et al., "The Alzheimer's Disease Neuroimaging Initiative," Neuroimaging Clinics of North America 15(4), pp. 869-877 (2005).
Nebrensky, et al., "A Particle Imaging and Analysis System for Underwater Holograms," Optical Methods and Data Processing in Heat and Fluid Flow, pp. 79-92 (2002).
Nelles, et al., "Dual-Source Parallel RF Transmission for Clinical MR Imaging of the Spine at 3.0 T: Intraindividual Comparison with Conventional Single-Source Transmission," Radiology 257(3), pp. 743-753 (2010).
Notice of Reasons for Refusal for Japanese Patent App. No. 2010-531335 dated Oct. 18, 2012, 6 pages (with translation).
Notice of Reasons for Refusal for Japanese Patent App. No. 2011-546331 dated Oct. 25, 2012, 6 pages (with translation).
Notice of Reasons for Refusal for Japanese Patent App. No. 2016-575179 dated Jan. 10, 2019, 9 pages (with translation).
Notice of Reasons for Refusal for Japanese Patent App. No. 2018-514278 dated Oct. 22, 2020, 9 pages (with translation).
Notification of Reason for Refusal for Korean Patent App. No. 10-2017-7002262 dated Jul. 17, 2020, 15 pages (with translation).
Obey & Vincent, "Novel Monodisperse "Silicone Oil"/Water Emulsions," Journal of Colloid and Interface Science 163(2), pp. 454-463 (1994).
Office Action for Chinese Patent App. No. 200880114008.3 dated Jul. 18, 2013, 25 pages (with translation).
Office Action for Chinese Patent App. No. 201410471610.X dated Mar. 22, 2016, 21 pages (with translation).
Omichi, et al., "Fabrication of enzyme-degradable and size-controlled protein nanowires using single particle nano-fabrication technique," Nature Communications 5, 3718, 8 pages (2014).
Orzada, et al., "Design and comparison of two eight-channel transmit/receive radiofrequency arrays for in vivo rodent imaging on a 7 T human whole-body MRI system," Medical Physics 37(5), pp. 2225-2232 (2010).
Pan, et al., "Three-Dimensional Particle Tracking for Dilute Particle-Liquid Flows in a Pipe," Measurement Science and Technology 13(8), pp. 1206-1216 (2002).
Panchal, et al., "Analyzing Subvisible Particles in Protein Drug Products: a Comparison of Dynamic Light Scattering (DLS) and Resonant Mass Measurement (RMM)," The AAPS Journal 16(3), pp. 440-451 (2014).
Parthasarathy, "Rapid, accurate particle tracking by calculation of radial symmetry centers," Nature Methods 9, pp. 724-726 (2012).
Pawashe & Sitti, "Two-dimensional vision-based autonomous microparticle manipulation using a nanoprobe," Journal of Micromechatronics 3(3-4), pp. 285-306 (2006).
Pedregosa, et al., "Scikit-learn: Machine Learning in Python," Journal of Machine Learning Research 12, pp. 2825-2830 (2011).
Perry, et al., "Real-space studies of the structure and dynamics of self-assembled colloidal clusters," Faraday Discussions 159, pp. 211-234 (2012).
Pine, et al., "Diffusing wave spectroscopy," Physical Review Letters 60(12), pp. 1134-1137 (1988).
Quick, "Integrated PET/MR," Journal of Magnetic Resonance Imaging 39(2), pp. 243-258 (2014).
Rappaz, et al., "Erythrocytes volume and refractive index measurement with a Digital Holographic Microscope," Proceedings of SPIE—The International Society for Optical Engineering 6445, 644509, 5 pages. (2007).
Rappaz, et al., "Simultaneous cell morphometry and refractive index measurement with dual-wavelength digital holographic microscopy and dye-enhanced dispersion of perfusion medium," Optics Letters 33(7), pp. 744-746 (2008).

(56) References Cited

OTHER PUBLICATIONS

Remsen, et al., "Analysis of Large Particle Count in Fumed Silica Slurries and Its Correlation with Scratch Defects Generated by CMP," Journal of the Electrochemical Society 153(5), pp. G453-G461 (2006).
Ripple & Dimitrova, "Protein particles: What we know and what we do not know," Journal of Pharmaceutical Sciences 101(10), pp. 3568-3579 (2012).
Roichman, et al., "Influence of Nonconservative Optical Forces on the Dynamics of Optically Trapped Colloidal Spheres: The Fountain of Probability," Physical Review Letters 101, 128301, 5 pages (2008).
Rubinstein, et al., "Recognition of distorted patterns by invariance kernels," Pattern Recognition 24(10), pp. 959-967 (1991).
Savin & Doyle, "Role of a finite exposure time on measuring an elastic modulus using microrheology," Physical Review E 71, 041106, 6 pages (2005).
Savin & Doyle, "Static and Dynamic Errors in Particle Tracking Microrheology," Biophysical Journal 88(1), pp. 623-638 (2005).
Schellekens, "Bioequivalence and the immunogenicity of biopharmaceuticals," Nature Reviews Drug Discovery 1, pp. 457-462 (2002).
Sciammarella, et al., "Measuring Mechanical Properties of Materials in the Micron Range," Optical Engineering 42(5), 8 pages (2003).
Seifi, et al., "Fast and accurate 3D object recognition directly from digital holograms," Journal of the Optical Society of America A 30(11), pp. 2216-2224 (2013).
Sheng, et al., "Digital holographic microscope for measuring three-dimensional particle distributions and motions," Applied Optics 45(16), pp. 3893-3901 (2006).
Shpaisman, et al., "Holographic microrefractometer," Applied Physics Letters 101, 091102, 3 pages (2012).
Siler & Cornish, "Measurement of Protein in Natural Rubber Latex," Analytical Biochemistry 229(2), pp. 278-281 (1995).
Singh, et al., "An industry perspective on the monitoring of sub-visible particles as a quality attribute for protein therapeutics," Journal of Pharmaceutical Sciences 99(8), pp. 3302-3321 (2010).
Siposova, et al., "Depolymerization of insulin amyloid fibrils by albumin-modified magnetic fluid," Nanotechnology 23(5), 055101, 10 pages(2012).
Sluzky, et al., "Kinetics of insulin aggregation in aqueous solutions upon agitation in the presence of hydrophobic surfaces," Proceedings of the National Academy of Sciences 88(21), pp. 9377-9381 (1991).
Smola & Scholkopf, "A tutorial on support vector regression," Statistics and Computing 14(3), pp. 199-222 (2004).
Sorensen, "Light Scattering by Fractal Aggregates: A Review," Aerosol Science and Technology 35(2), pp. 648-687 (2001).
Strzodka, et al., "Real-Time Motion Estimation and Visualization on Graphics Cards," IEEE Visualization 2004, pp. 545-552 (2004).
Tolla & Boldridge, "Distortion of Single-Particle Optical Sensing (SPOS) Particle Count by Sub-Countable Particles," Particle & Particle Systems Characterizaion 27(1-2), pp. 21-31 (2010).
Voros, "The Density and Refractive Index of Adsorbing Protein Layers," Biophysical Journal 87(1), pp. 553-561 (2004).
Wang, "Protein aggregation and its inhibition in biopharmaceutics," International Journal of Pharmaceutics 289(1-2), pp. 1-30 (2005).
Wang, et al., "Celebrating Soft Matter's 10th Anniversary: Monitoring colloidal growth with holographic microscopy," Soft Matter 11(6), pp. 1062-1066 (2015).
Wang, et al., "Holographic characterization of protein aggregates," Journal of Pharmaceutical Sciences 105(3), pp. 1074-1085 (2016).
Wang, et al., "Stimulus-responsive colloidal sensors with fast holographic readout," Applied Physics Letters 107(5), 051903, 5 pages (2015).
Wang, et al., "Using the discrete dipole approximation and holographic microscopy to measure rotational dynamics of non-spherical colloidal particles," Journal of Quantitative Spectroscopy and Radiative Transfer 146, pp. 499-509 (2014).
Weber, et al., "A Novel 8-Channel Transceive Volume-Array for a 9.4T Animal Scanner," Proceedings of the International Society for Magnetic Resonance in Medicine 16, p. 151 (2008).
Weinbuch, et al., "Micro-Flow Imaging and Resonant Mass Measurement (Archimedes)-Complementary Methods to Quantitatively Differentiate Protein Particles and Silicone Oil Droplets," Journal of Pharmaceutical Sciences 102(7), pp. 2152-2165 (2013).
Witten & Sander, "Diffusion-Limited Aggregation, a Kinetic Critical Phenomenon," Physical Review Letters 47(19), pp. 1400-1403 (1981).
Written Opinion for Singapore Patent App. No. 11201802181R dated Mar. 28, 2019, 7 pages.
Wu, et al., "Synthesis of mesoporous silica nanoparticles," Chemical Society Reviews 42(9), pp. 3862-3875 (2013).
Xiao & Grier, "Multidimensional Optical Fractionation of Colloidal Particles with Holographic Verification," Physical Review Letters 104, 028302, 4 pages (2010).
Yang, et al., "Spatial coherence of forward-scattered light in a turbid medium," Journal of the Optical Society of America A 16(4), pp. 866-871 (1999).
Ye, et al., "Accelerating Magnetic Resonance Fingerprinting (MRF) Using t-Blipped Simultaneous Multislice (SMS) Acquisition," Magnetic Resonance in Medicine 75(5), pp. 2078-2085 (2016).
Yevick, et al., "Machine-learning approach to holographic particle characterization," Optics Express 22(22), pp. 26884-26890 (2014).
Yip, et al., "Atomic Force Microscopy of Crystalline Insulins: The Influence of Sequence Variation on Crystallization and Interfacial Structure," Biophysical Journal 74(5), pp. 2199-2209 (1998).
Yip, et al., "Structural and Morphological Characterization of Ultralente Insulin Crystals by Atomic Force Microscopy: Evidence of Hydrophobically Driven Assembly," Biophysical Journal 75(3), pp. 1172-1179 (1998).
Zolls, et al., "How subvisible particles become invisible—relevance of the refractive index for protein particle analysis," Journal of Pharmaceutical Sciences 102(5), pp. 1434-1446 (2013).
Agarwal, et al., "Manipulation and assembly of nanowires with holographic optical traps," Optics Express 13(22), pp. 8906-8912 (2005).
Arlt, et al., "Optical micromanipulation using a Bessel light beam," Optics Communications 197(4-6), pp. 239-245 (2001).
Ashkin, "History of optical trapping and manipulation of small-neutral particle, atoms, and molecules," IEEE Journal of Selected Topics in Quantum Electronics 6(6), pp. 841-856 (2000).
Ashkin, "Optical trapping and manipulation of neutral particles using?lasers," Proceedings of the National Academy of Sciences 94(10), pp. 4853-4860 (1997).
Ashkin, et al., "Observation of as single-beam gradient force optical trap for dielectric particles," Optics Letters 11(5), pp. 288-290 (1986).
Biancaniello, et al., "Colloidal Interactions and Self-Assembly Using DNA Hybridization," Physical Review Letters 94(5):058302, 4 pages (2005).
Cizmar, et al., "Sub-micron particle organization by self-imaging of non-diffracting beams," New Journal of Physics 8(43), 23 pages (2006).
Cojoc, et al., "Lasertrapping and micro-manipulation using optical vortices," Microelectronic Engineering 78-79, pp. 125-131 (2005).
Crocker & Grier, "Microscopic measurement of the pair interaction potential of charge-stabilized colloid," Physical Review Letters 73(2), pp. 352-355 (1994).
Crocker, et al., "Entropic Attraction and Repulsion in Binary Colloids Probed with a Line Optical Tweezer," Physical Review Letters 82(21), pp. 4352-4355 (1999).
Curtis & Grier, "Modulated optical vortices," Optics Letters 28(11), pp. 872-874 (2003).
Curtis & Grier, "Structure of Optical Vortices," Physical Review Letters 90(13):133901, 4 pages (2003).
Curtis, et al., "Dynamic holographic optical tweezers," Optics Communications 207(1-6), pp. 169-175 (2002).
Duda & Hart, "Use of the Hough transformation to detect lines and curves in pictures," Communications of the ACM 15(1), pp. 11-15 (1972).

(56) References Cited

OTHER PUBLICATIONS

Duffy, et al., "Rapid Prototying of Microfluidic Systems in Poly(dimethylsiloxane)," Analytical Chemistry 70(23), pp. 4974-4984 (1998).
Dufresne & Grier, "Optical tweezer arrays and optical substrates created with diffractive optics," Review of Scientific Instruments 69(5), pp. 1974-1977 (1998).
Dufresne, et al., "Computer-generated holographic optical tweezer arrays," Review of Scientific Instruments 72(3), pp. 1810-1816 (2001).
Eriksen, et al., "Fully dynamic multiple-beam optical tweezers," Optics Express 10(14), pp. 597-602 (2002).
Faucheux, et al., "Optical Thermal Ratchet," Physical Review Letters 74(9), pp. 1504-1507 (1995).
Faucheux, et al., "Periodic forcing of a Brownian particle," Physical Review E 51(6), pp. 5239-5250 (1995).
Gahagan & Swartzlander, "Optical vortex trapping of particles," Optics Letters 21(11), pp. 827-829 (1996).
Gleeson, et al., "Analytical approach to sorting in periodic and random potentials," Physical Review E 73(4):041102, 9 pages (2006).
Gopinathan & Grier, "Statistically Locked-In Transport through Periodic Potential Landscapes," Physical Review Letters 92(13):130602, 4 pages (2004).
Grier & Roichman, "Holographic optical trapping," Applied Optics 45(5), pp. 880-887 (2006).
Grier, "Optical tweezers in colloid and interface science," Current Opinion in Colloid & Interface Science 2(3), pp. 264-270 (1997).
He, et al., "Optical Particle Trapping with Higher-order Doughnut Beams Produced Using High Efficiency Computer Generated Holograms," Journal of Modern Optics 42(1), pp. 217-223 (1995).
Hermann, et al., "Separation of suspended patricles in microfluidic systems by directional-locking in periodic fields," Physical Review E 79(6):061404, 9 pages (2009).
Hirai, et al., "Laser Photophoresis of a Single Droplet in Oil in Water Emulsions," Langmuir 12(23), pp. 5570-5575 (1996).
Korda, et al., "Kinetically Locked-In Colloidal Transport in an Array of Optical Tweezers," Physical Review Letters 89(12): 128301, 4 pages (2002).
Lacasta, et al., "Sorting mesoscopic particles driven through periodic potential landscapes," Modern Physics Letters B 20(23), pp. 1427-1442 (2006).
Ladavac, et al., "Sorting mesoscopic objects with periodic potential landscapes: Optical fractionation," Physical Review E 70(1):010901, 4 pages (2004).
Lee & Grier, "One-dimensional optical thermal ratchets," Journal of Physics: Condensed Matter 17(47), 7 pages (2005).
Lee & Grier, "Robustness of holographic optical traps against phase scaling errors," Optics Express 13(19), pp. 7458-7465 (2005).
Lee, et al., "Optical solenoid beams," Optics Express 18(7), pp. 6988-6993 (2010).
Liesner, et al., "Multi-functional optical tweezers using computer-generated holograms," Optics Communications 185(1-3), pp. 77-82 (2000).
Ma, et al., "Determination of complex refractive index of polystyrene microspheres," Physics in Medicine & Biology 48, pp. 4165-4172 (2003).
MacDonald, et al., "Microfluidic sorting in an optical lattice," Letters to Nature 426, pp. 412-424 (2003).
Messmer, et al., "GPULib: GPU Computing in High-Level Languages," Computing in Science & Engineering 10(May 2008), pp. 70-73 (2008).
Milne, et al., "Fractionation of polydisperse colloid with acousto-optically generated potential enery landscapes," Optics Letters 32(9), pp. 1144-1146 (2007).
Owens, et al., "A Survey of General-Purpose Computation on Graphics Hardware," Computer Graphics Forum 26(1), pp. 80-113 (2007).
Pelton, et al., "Transport and fractionation in periodic potential-energy landscapes," Physical Review E 70(3):031108, 11 pages (2004).
Polin, et al., "Optimized holographic optical traps," Optics Express 13(15), pp. 5831-5845 (2005).
Rodrigo, et al., "Four-dimensional optical manipulation of colloidal particles," Applied Physics Letters 86(7):074103, 3 pages (2005).
Roichman, et al., "Colloidal transport through optical tweezer arrays," Physical Review E 75:011407, 4 pages (2007).
Roichman, et al., "Optical Forces Arising from Phase Gradients," Physical Review Letters 100:031602, 4 pages (2008).
Roichman, et al., "Optical traps with geometric aberrations," Applied Optics 45(15), pp. 3425-3429 (2006).
Roichman, et al., "Volumetric imaging of holographic optical traps," Optics Express 14(22), pp. 10907-10912 (2006).
Sancho, et al., "Particle separation by external fields on periodic surfaces," Journal of Physics: Condensed Matter 17, pp. SF4151-SF4163, (2005).
Sasaki, et al., "Pattern formation and flow control of fine particles by laser-scanning micromanipulation," Optics Letters 16(19), pp. 1463-1465 (1991).
Simpson, et al., "Optical tweezers and optical spanners with Laguerre-Gaussian modes," Journal of Modern Optics 43(122), pp. 2485-2491 (1996).
Sundbeck, et al., "Structure and scaling of helical modes of light," Optics Letters 30(5), pp. 477-479 (2005).
Svoboda & Block, "Biological Applications of Optical Forces," Annual Review of Biophysics and Biomolecular Structure 23(1), pp. 247-285 (1994).
Verma, et al., "Entropic Colloidal Interactions in Concentrated DNA Solutions," Physical Review Letters 81(18), pp. 4004-4007 (1998).
Xiao & Grier, "Sorting colloidal particles into multiple channels with optical forces: Prismatic optical fractionation," Physical Review E 82(5):051407, 9 pages (2010).
Yu, et al., "The manipulation and assembly of CuO nanorods with line optical tweezers," Nanotechnology 15(12), pp. 1732-1736 (2004).
Zhao, et al., "Recording and reconstruction of a color holographic image by using digital lensless Fourier transform holography," Optics Express 16(4), pp. 2514-2519 (2008).
Butime, et al., "Conoscopic holograms analysis using variations of the Hough transform," International Journal of Imaging Systems and Technology 19(1), pp. 10-13 (2009).

\* cited by examiner

Figure 4A  Figure 4B  Figure 4C  Figure 4D
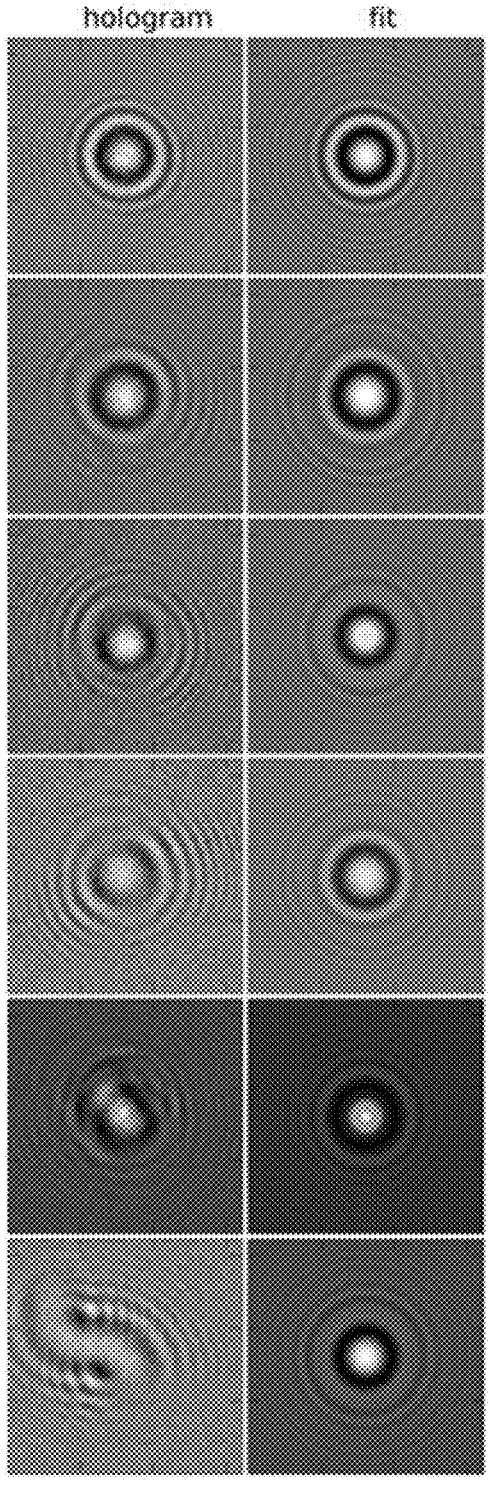
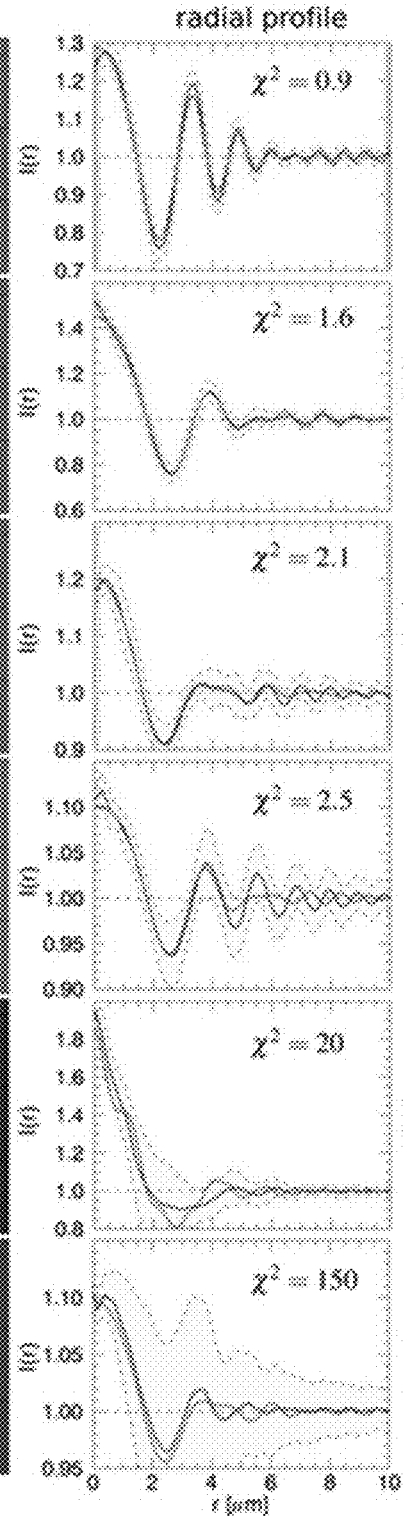
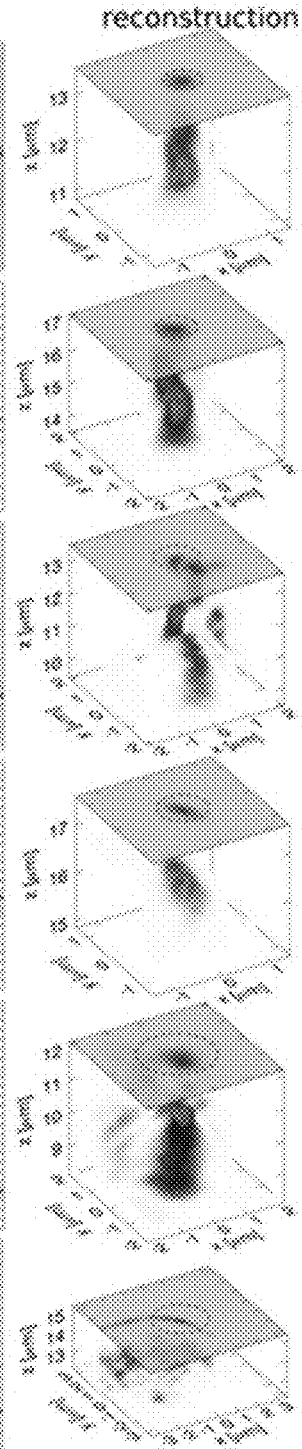

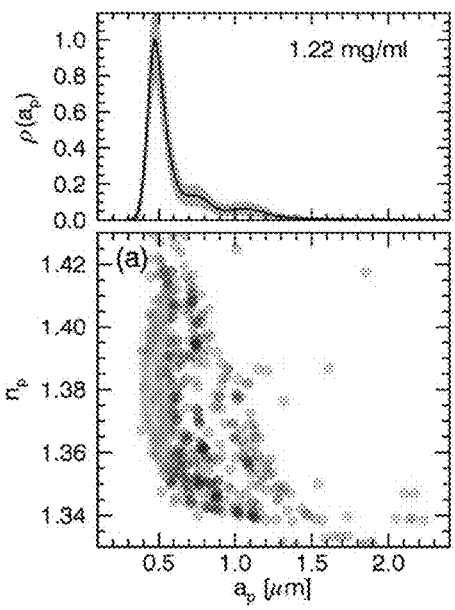
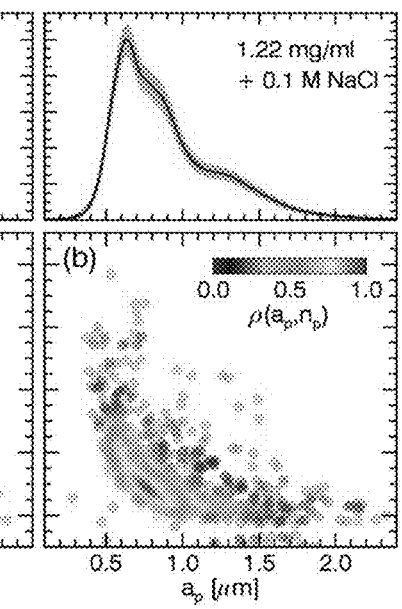
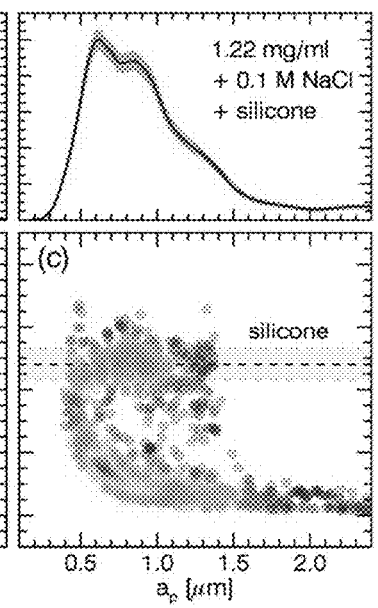
Figure 5B     Figure 5D     Figure 5F
Figure 5A     Figure 5C     Figure 5E

HOLOGRAPHIC CHARACTERIZATION OF PROTEIN AGGREGATES

CROSS-REFERENCE TO RELATED APPLICATIONS

This application is a continuation of U.S. patent application Ser. No. 16/076,265, which is the U.S. National Phase of PCT/US2017/016857, filed Feb. 7, 2017, which claims priority to and the benefit of U.S. Provisional Patent App. No. 62/292,842 filed Feb. 8, 2016, the entire contents of which are incorporated herein by reference.

STATEMENT OF GOVERNMENT INTEREST

This invention was made with government support under grant numbers DMR1420073 and DMR0922680 awarded by the National Science Foundation to New York University. The government has certain rights in the invention.

BACKGROUND OF THE INVENTION

Proteins and protein aggregates are increasingly important for commercial applications. Characterization of protein aggregates provides a challenge, particular for large-scale implementation and with regard to real-time or near real-time characterization. The tendency of proteins to aggregate into clusters is a major concern in manufacturing protein-based bio-pharmaceuticals and assessing their safety. In addition to reducing therapeutic efficacy, protein aggregates elicit immune responses that result in clinical adverse events with the potential to compromise the health of affected individuals. Detecting, counting and characterizing protein aggregates is essential to understanding the critical pathways responsible for protein aggregation. Established particle characterization technologies such as dynamic light scattering work well for in situ characterization of sub-micrometer-scale aggregates. Others, such as micro-flow imaging, work best for visible aggregates larger than five micrometers or so. Comparatively few established techniques probe the subvisible range from 100 nm to 10 μm. The need for enhanced characterization techniques is particularly acute in applications that require real-time monitoring of subvisible aggregates in their native environment.

The tendency of proteins to cluster and the ability to detect and characterize such is an important consideration. There exists a need for systems and methods to accurately and quickly characterize proteins.

SUMMARY OF THE INVENTION

One embodiment relates to a method of characterizing a sample of plurality of protein aggregates. The method includes flowing the sample through an observation volume of a holographic microscope. A first set of holograms is generated based upon holographic video microscopy of a first set of protein aggregates within the observation volume at a first time. Each of the protein aggregates of the first set of protein aggregate is modeled as a sphere. The refractive index and the radius for each of the protein aggregates of the first set of protein aggregates is determined. A second set of holograms is generated based upon holographic video microscopy of a second set of protein aggregates within the observation volume at a second time. Each of the protein aggregates of the second set of protein aggregate is modeled as a sphere. The refractive index and the radius are determined for each of the protein aggregates of the second set of protein aggregates.

Another embodiment relates to a method of characterizing a plurality of protein aggregates. Holograms of protein aggregates of the plurality of protein aggregates are generated, each hologram based upon holographic video microscopy of a protein aggregate $P_N$ of the plurality of protein aggregates at a time TN. The refractive index and the radius of the protein aggregate $P_N$ are determined at the time TN. The change in the plurality of protein aggregates over time is characterized based upon the determined refractive index and radius of the particles.

Another embodiment relates to a computer-implemented machine for characterizing a plurality of protein aggregates, comprising: a processor, a holographic microscope comprising a coherent light, a specimen stage having an observation volume, an objective lens, and an image collection device. The holographic microscope is in communication with the processor. The system further comprises a tangible computer-readable medium operatively connected to the processor and including computer code. The computer code is configured to: control the flow of the sample through an observation volume of the holographic microscope; receive a first set of holograms based upon holographic video microscopy of a first set of protein aggregates within the observation volume at a first time; model each of the protein aggregates of the first set of protein aggregate as a sphere; determine the refractive index and the radius for each of the protein aggregates of the first set of protein aggregates; receive a second set of holograms based upon holographic video microscopy of a second set of protein aggregates within the observation volume at a second time; model each of the protein aggregates of the second set of protein aggregate as a sphere; and determine the refractive index and the radius for each of the protein aggregates of the second set of protein aggregates.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIGS. 4A-4D show the influence of aggregate morphology on holographic characterization. Holograms of typical aggregates arranged in order of increasing discrepancy between measured and fit holograms. FIG. 4A shows 160 pixel×160 pixel regions of interest from the microscope's field of view, centered on features automatically identified as candidate BSA-PAH complexes. FIG. 4B shows fits to the Lorenz-Mie theory for holograms formed by spheres. FIG. 4C shows radial profiles of the experimental hologram (black curves) overlaid with the radial profile of the fits (red curves). Shaded regions represent the estimated experimental uncertainty. FIG. 4D shows Rayleigh-Sommerfeld reconstructions of the aggregates' three-dimensional structures obtained from the experimental holograms. Grayscale images are projections of the reconstructions, which resemble equivalent bright-field images at optimal focus. Superimposed circles indicate fit estimates for the particle size.

FIGS. 5A-5F illustrate the impact of contaminants on the measured distribution of the radius $a_p$ and refractive index $n_p$ of BSA-PAH complexes. FIG. 5A (refractive index) and FIG. 5B (size distribution) illustrate results for BSA complexed with PAH in Tris buffer (1100 aggregates). FIG. 5C (refractive index) and FIG. 5D (size distribution) illustrate results for same sample of FIGS. 5A and 5B but with 0.1 M NaCl (1200 aggregates); FIG. 5E (refractive index) and FIG. 5F (size distribution) illustrate results for a sample prepared under the same conditions as FIGS. 5C and 5D with added silicone spheres (1600 features). Each point in the scatter plots (FIGS. 5A, 5C, and 5E) represents the properties of a single aggregate and is colored by the relative density of observations, $p(a_p, n_p)$. FIGS. 5B, 5D, and 5F present the associated size distribution $p(a_p)$ within a shaded region representing the instrumental and statistical error

FIG. 8A shows a sample without added salt (sample of FIGS. 5A-5B). FIG. 8B shows a sample with added NaCL (sample of FIGS. 5C-5D).

FIG. 10A shows a monodisperse sample (600 spheres). FIG. 10B shows a polydisperse sample (600 spheres).

FIG. 11A shows a sample prepared under the same conditions as in FIGS. 5A-5B spiked with the monodisperse spheres from FIG. 10A (2000 features). FIG. 11B shows a sample prepared under the same conditions as in FIG. 5C-5D spiked with the polydisperse spheres from FIG. 10B (1600 features). FIGS. 11C and 11D show the projected relative probability density, $r(a_p)$, for particle radius from the data in FIG. 11A and FIG. 11B, respectively.

FIG. 12A shows 1 mg/mL in Human IgG PBS buffer, FIG. 12B shows 3 mg/mL silicone oil in PBS buffer. These samples were mixed together as shown in FIG. 12C, with final concentrations of 0.5 mg/mL Human IgG and 1.5 mg/mL of silicone oil in PBS buffer. All measurements were done using a 40× objective (Nikon 0.75NA) and a 100 μm depth microfluidic channel (μ-Slide VI 0.1 Uncoated)

DETAILED DESCRIPTION OF THE PREFERRED EMBODIMENTS

Figures 1A, 1B:
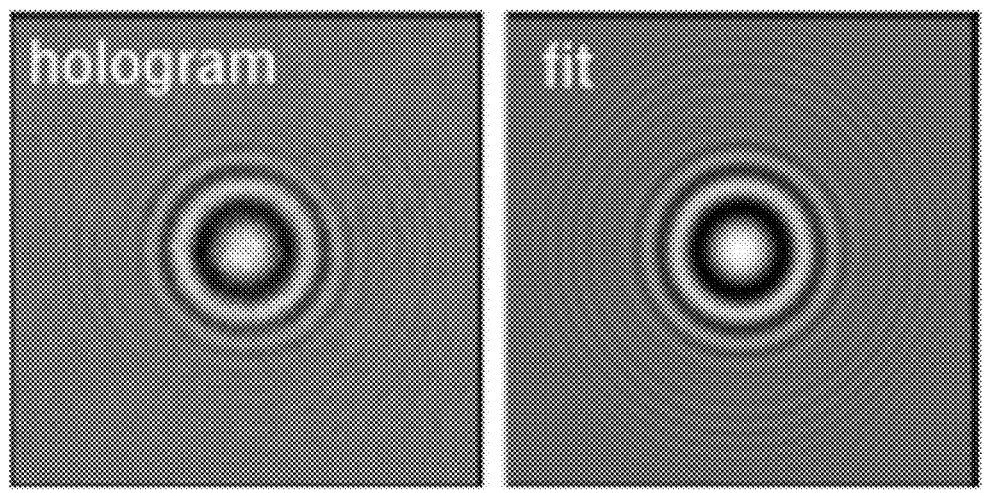
FIG. 1A illustrates a measured holograph of a 1 micrometer diameter BSA aggregate.
FIG. 1B illustrates a fit based upon Lorenz-Mie theory of light scattering.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

Holographic characterization of fractal protein aggregates yields insights into the size and refractive index of individual aggregates in solution. Single-aggregate characterization data can be combined into the joint distribution for size and refractive index in a dispersion of aggregates, without a priori assumptions about the nature of the distribution. Interpreting the measured size-index joint distribution for an ensemble of protein aggregates in terms of an effective-medium model for scattering by fractal aggregates yields an estimate for the aggregates' mean fractal dimension, and therefore their morphology. When this interpretation is applied to dispersions of aggregated bovine serum albumin, the extracted fractal dimension, D=1.2 agrees with previous reports based on ex situ measurement techniques such as electron microscopy and atomic force microscopy. The success of this population-averaged scaling analysis lends confidence to the single-aggregate characterization data on which it is based, and thus to the novel proposal that holographic characterization can be used to analyze the size, structure and morphology of micrometer-scale protein aggregates.

The tendency of proteins to aggregate into clusters is implicated in disease processes, and also affects the efficacy of protein-based pharmaceuticals. Here, a method is introduced based on holographic video microscopy for detecting, counting and characterizing individual protein aggregates that rapidly builds up population statistics on subvisible aggregates in solution in their natural state, without dilution or special solvent conditions, and without the need for chemical or optical labels. The use of holographic video microscopy, including Lorenz-Mie analysis is known for the characterization of spherical homogenous particles. Protein aggregates present a unique challenge in that they are both not homogenous and not spherical. Protein aggregates tend to be irregularly shaped, and can be highly branched spindly structures. Described herein are systems and methods that utilize a determination of the properties of an effective sphere, one that includes the aggregate and the surrounding and interstitial fluid medium. The estimates of radius and refractive index of this defined sphere are then adjusted to those of the actual protein aggregate through the use of modeling, such as the fractal model. In one application, the systems and methods are utilized without characterization of the materials, but rather to provide information regarding "counting" of the protein aggregates in their native environment, in one embodiment in near real time.

The proof of concept examples of this method are made through measurements on aggregates of bovine serum albumin (BSA) and bovine insulin (BI) over the range of radii from 300 nm to 10 µm. Accumulating particle-resolved measurements into joint distributions for the aggregates' size and refractive index offers insights into the influence of growth conditions on the mechanism of protein aggregation. A scaling analysis of this joint distribution yields estimates for the aggregates' fractal dimension that are consistent with previous ex situ measurements and so offers insights into the aggregates' morphology. The success of this scaling analysis suggests that the results for single-cluster sizes and refractive indexes accurately reflect the properties of the individual aggregates.

Figure 2:
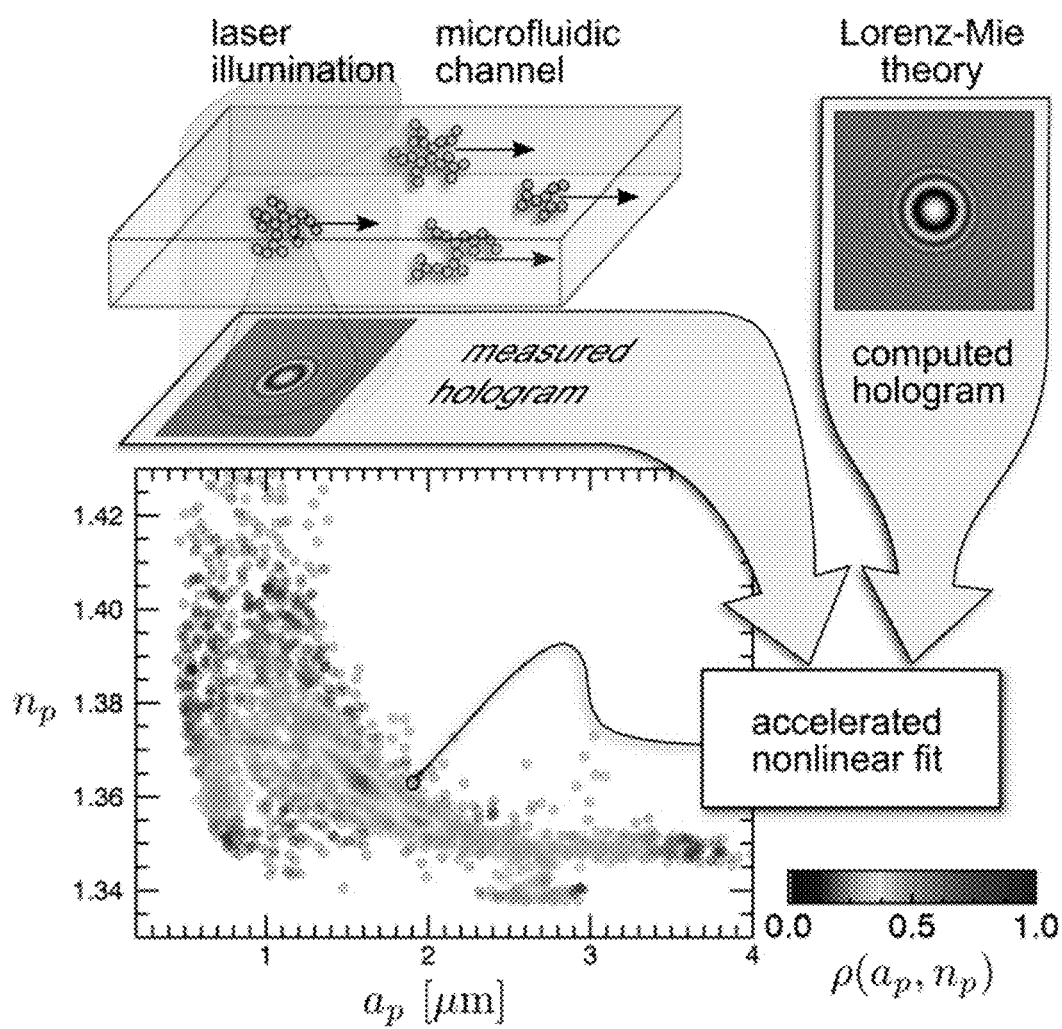
FIG. 2 shows protein aggregates flowing down a microfluidic channel form holograms as they pass through a laser beam. A typical experimental hologram is reproduced as a grayscale image in the figure. Each hologram is recorded by a video camera and compared with predictions of Lorenz-Mie theory to measure each aggregate's radius, $a_p$, and refractive index, $n_p$. The inset scatter plot shows experimental data for 3000 subvisible aggregates of bovine insulin, with each data point representing the properties of a single aggregate, and colors denoting the relative probability density $p(a_p, n_p)$ for observations in the $(a_p, n_p)$ plane.

The measurement technique, such as the embodiment of FIG. 2, is based on in-line holographic video microscopy a technique that creates holograms of individual objects in the microscope's field of view. A holographic microscope illuminates its sample with a collimated laser beam rather than a conventional incoherent light source. Light scattered by a small object, such as a protein aggregate, therefore interferes with the remainder of the beam in the focal plane of an optical microscope. The microscope magnifies the interference pattern and projects it onto the face of a video camera, which records the spatially varying intensity pattern, l(r). Each image in the resulting video stream is a holographic snapshot of the scatterers passing through the laser beam, and can be analyzed with predictions based on the Lorenz-Mie theory of light scattering to measure each aggregate's radius $a_p$, refractive index, $n_p$, and three-dimensional position, $r_p$. Holographic characterization originally was developed for analyzing spherical particles (see, e.g., Lee S H, Roichman Y, Yi G R, Kim S H, Yang S M, van Blaaderen A, et al. Characterizing and tracking single colloidal particles with video holographic microscopy. Opt Express. 2007; 15:18275-18282, incorporated herein by reference). Rigorously generalizing the analysis to account for the detailed structure of aspherical and inhomogeneous objects is prohibitively slow because of the analytical complexity and the associated computational burden. The idealized spherical model is used to characterize protein aggregates with the understanding that the results should be interpreted as referring to an effective sphere comprising both the protein aggregate and the fluid medium that fills out the effective sphere.

FIG. 2 illustrates a protein aggregates flowing down a microfluidic channel form holograms as they pass through a laser beam. A typical experimental hologram is reproduced as a grayscale image in the figure. Each hologram is recorded by a video camera and compared with predictions of Lorenz-Mie theory to measure each aggregate's radius, $a_p$, and refractive index, $n_p$. The scatter plot shows experimental data for 3000 subvisible aggregates of bovine insulin, with each data point representing the properties of a single aggregate, and colors denoting the relative probability density $p(a_p, n_p)$ for observations in the $(a_p, n_p)$ plane.

In one embodiment, the holographic characterization system and methods provide for detection of protein aggregates having a radius in of an acceptable size range, such as within the range of 200 nm (300 nm, 400 nm, 500 nm) to 20 µm (10 µm, 1 µm, 900 nm, 800 nm). Further, embodiments enable counting of protein aggregates within the size range, allowing determination of the number density of the protein aggregates (in the size range). In addition, the systems and methods allow for identification of protein aggregates within sub-ranges of the acceptable size range. Some techniques, such as dynamic light scattering (DLS) cover the lower end of the same size range and can probe particles that are smaller. Other techniques, such as microflow imaging (MFI) operate at the upper end of the same size range, and can probe particles that are still larger. The present approach to holographic characterization bridges the operating domains of these other techniques. The specified range reflects the current implementation and can be extended through the choice of optical hardware and through modification of the software used to analyze holograms. The lower end of the range is limited also by the wavelength of light. The upper end of the range is not fundamentally limited in this way, but can be limited in practice by considerations of computational complexity.

In order to accomplish the holographic characterization, in one embodiment the system and methods characterize protein aggregates in the acceptable size range. Characterization includes: a) measuring the radius with Lorenz-Mie analysis; b) measuring the effective refractive index of the aggregate with Lorenz-Mie analysis; c) estimating the porosity of an individual aggregate based on its effective refractive index relative to that of the protein itself; d) estimating the mean porosity of an ensemble of aggregates based on the shape of the distribution of single-particle characterization data (using Eq. (1) set forth below), assuming that the aggregates may be modeled as having a fractal geometry); e) measuring an individual aggregate's morphology based on back-propagation of the aggregate's hologram. In a further embodiment, the back-propagation step is a distinct and parallel path for analyzing the same data, and may include 1) Fresnel back-propagation, 2) Rayleigh-Sommerfeld back-propagation and/or 3) Rayleigh-Sommerfeld deconvolution. This term effective refractive index refers the refractive index of the material within a spherical volume that incorporates both the particle under study and also the medium intercalated within that particle. This "effective sphere" has a size and a refractive index that reflect the corresponding properties of the particle of interest. This particle could be a colloidal sphere, an aspherical colloidal particle, an aggregates of colloidal particles, or an aggregate of molecules such as a protein aggregate. The measured effective refractive index is neither the refractive index of the medium, nor of a pure protein cluster, but a composite of all of the components of the aggregate. When there is more solvent, incorporated in the aggregate, the effective refractive index will be closer to the solvent refractive index, and when there is less solvent, it will be further from the solvent refractive index. The effective index of refraction provides information about the proportion of the effective sphere's volume that is filled with the medium, and therefore provides useful insight into the particle's morphology.

With reference to the embodiment of FIG. 2, The holographic characterization instrument uses a conventional microscope objective lens (Nikon Plan Apo, 100×, numerical aperture 1.45, oil immersion), which, in combination with a standard tube lens, yields a system magnification of 135 nm/pixel on the face of a monochrome video camera (NEC TI-324AII). The sample is illuminated with the collimated beam from a solid state laser (Coherent Verdi) delivering 10 mW of light to the sample vacuum wavelength of 532 nm. This light is spread over the 3 mm diameter of the beam, in this example, yielding a peak irradiance of 1.5 mW/mm$^2$. For micrometer-scale colloidal spheres, this instrument can measure an individual particle's radius with nanometer precision, its refractive index to within a part per thousand, and can track its position to within a nanometer in the plane and to within 3 nanometers along the optical axis. Each fit can be performed in a fraction of a second, for example a few tens of milliseconds, using automated feature detection and image recognition algorithms. A single fit suffices to characterize a single protein aggregate.

To characterize the population of aggregates in a protein dispersion, the sample is flowed through the microscope's observation volume in a microfluidic channel. Given the camera's exposure time of 0.1 ms, results are immune to motion blurring for flow rates up to 100 μm/s. Under typical conditions, no more than ten protein aggregates pass through the 86 μm×65 μm field of view at a time. These conditions simplify the holographic analysis by minimizing overlap between individual particles' scattering patterns. Each particle typically is aggregate typically is recorded in multiple video frames as it moves through the field of view. Such sequences of measurements are linked into trajectories using a maximum-likelihood algorithm and median values are reported for each trajectory. These considerations establish an upper limit to the range of accessible aggregate concentrations of $10^8$ aggregates/ml. At the other extreme, 10 min of data suffices to detect, count and characterize aggregates at concentrations as low as $10^4$ aggregates/ml. This sensitivity compares favorably with both dynamic light scattering and nanoparticle tracking analysis. In one embodiment, a data set consisting of 5000 particles can be acquired in about 5 min.

The scatter plot inset into FIG. 2 shows typical results for subvisible aggregates of bovine insulin. Each point represents the properties of a single aggregate, and is comparable in size to the estimated errors in the radius and refractive index. Colors represent the local density $p(a_p, n_p)$ of recorded data points in the $(a_p, n_p)$ plane, computed with a kernel density estimator, with red indicating the most probable values.

Holographic characterization can be generalized to accommodate aspherical and inhomogeneous particles. The associated light-scattering calculations are computationally burdensome, however. Protein aggregates are characterized using the light-scattering theory for isotropic and homogeneous spheres with the understanding that the aggregates may depart from this idealized model. The typical example in FIG. 1, however, demonstrates that the spherical model accounts well for observed single-particle scattering patterns in the system.

Calibrating the Holographic Characterization Instrument

Holographic characterization relies on four instrumental calibration parameters: the vacuum wavelength of the laser illumination, the magnification of the optical train, the dark count of the camera, and the single-pixel signal-to-noise ratio at the operating illumination level. All of these can be measured once and then used for all subsequent analyses.

The vacuum wavelength of the laser is specified by the manufacturer and is independently verified to four significant figures using a fiber spectrometer (Ocean Optics, HR4000). The microscope's system magnification is measured to four significant figures using a precision micrometer scale (Ted Pella, catalog number 2285-16). The camera's dark count is measured by blocking the laser illumination and computing the average image value at each pixel. Image noise is estimated from holographic images with the median-absolute-deviation (MAD) metric.

In addition to these instrumental calibrations, obtaining accurate results also requires an accurate value for the refractive index of the medium at the laser wavelength and at the sample temperature. For the aqueous buffers in the present study, this value was obtained to four significant figures with an Abbe refractometer (Edmund Optics). Approximating this value with the refractive index of pure water, nm=1.335, at the measurement temperature of 21±1° C. yields systematic errors in the estimated radius and refractive index of no more than 0.1%.

Operating Range of Holographic Characterization

The operating range of the holographic characterization instrument is established by measurements on aqueous dispersions of colloidal spheres intended for use as particle size standards. The interference fringes in each particle's holograms must be separated by at least one pixel in the microscope's focal plane. This requirement is accommodated by setting the focal plane 5 μm below the glass-water interface in the sample cell. The largest accessible axial displacement is set both by the need to fit multiple concentric fringes into the camera's field of view, and also by the reduction of image contrast below the camera's noise floor. This upper limit is roughly 100 μm for this instrument. In a preferred embodiment, the samples are passed through microfluidic channels with an optical path length of 30 μm to ensure good imaging conditions for all aggregates, regardless of their height in the channel.

The lower end of the range of detectable particle sizes is limited to half the wavelength of light in the medium. Particles smaller than this yield detectable holograms, which can be fit by Lorenz-Mie theory. These fits, however, do not cleanly separate the particle size from the refractive index. If the particle's refractive index is known a priori, these measurements again can yield reliable estimates for the particle's radius. For the example embodiment, the practical lower limit is set by the 8-bit dynamic range of the camera to $a_p > 200$ nm. Smaller particles' light-scattering patterns lack the contrast needed for reliable detection and characterization.

For the example embodiment, the upper size limit is set to $a_p < 10$ μm by the depth of the channel. The described example setup is not expected to be able to reliably observe and correctly identify irregularly shaped protein aggregates much larger than 10 μm. Large transient aggregates are likely to be broken up by hydrodynamic shearing in the Poiseuille flow within the channel. Highly asymmetric aggregates substantially larger than the wavelength of light are likely to be misidentified as two or more distinct features by the feature-identification algorithm developed for automated holographic characterization of spheres. No effort is made to correct for this artifact, although its presence is confirmed by comparing results from holographic characterization with results obtained by reanalyzing the same data for micro-flow imaging using the methods from the next section.

Holographic Morphology Measurements

The same holograms used for holographic characterization through Lorenz-Mie analysis also can be used to visualize the three-dimensional morphology of individual aggregates through Rayleigh-Sommerfeld back-propagation with volumetric deconvolution. This technique uses the Rayleigh-Sommerfeld diffraction integral to reconstruct the volumetric light field responsible for the observed intensity distribution. The object responsible for the scattering pattern appears in this re-construction in the form of the caustics it creates in the light field. For objects with features comparable in size to the wavelengths of light, these caustics have been shown to accurately track the position and orientation of those features in three dimensions. Deconvolving the resulting volumetric data set with the point-spread function for the Rayleigh-Sommerfeld diffraction kernel eliminates twin-image artifacts and yields a three-dimensional representation of the scatterer.

Volumetric reconstructions of protein aggregates can be projected into the imaging plane to obtain the equivalent of bright-field images in the plane of best focus. This reaps the benefit of holographic microscopy's very large effective depth of focus compared with conventional bright-field microscopy. The resulting images are useful for micro-flow imaging analysis, including analysis of protein aggregates' morphology. This information, in turn, can be used to assess the rate of false feature identifications in the Lorenz-Mie analysis, and thus the rate at which larger aggregates are misidentified as clusters of smaller aggregates.

Investigating aggregate morphology with holographic deconvolution microscopy is a useful complement to holographic characterization through Lorenz-Mie analysis. Whereas Lorenz-Mie fits proceed in a matter of milliseconds, however, Rayleigh-Sommerfeld back-propagation is hundreds of times slower. This study focuses, therefore, on the information that can be obtained rapidly through Lorenz-Mie Characterization.

EXAMPLES

Material Preparation

Samples of bovine pancreas insulin (Mw: 5733.49 Da, Sigma-Aldrich, CAS number: 11070-73-8) were prepared according to previously published methods with modifications for investigating insulin aggregation induced by agitation alone. Insulin was dissolved at a concentration of 5 mg/ml in 10 mM Tris-HCl buffer (Life Technologies, CAS number 77-86-1) whose pH was adjusted to 7.4 with 37% hydrochloric acid (Sigma Aldrich, CAS number: 7647-01-0). The solution then was centrifuged at 250 rpm for 1 h to induce aggregation, at which time the sample still appeared substantially transparent.

Solutions of bovine serum albumin (BSA) (Mw: 66 500 Da, Sigma Aldrich, CAS number: 9048-46-8) were aggregated by complexation with poly(allylamine hydrochloride) (PAH) (Mw: 17 500 g/mol, CAS number: 71550-12-4, average degree of polymerization: 1207) [33, 34]. BSA and PAH were dissolved in 10 mM Tris buffer (Life Technologies, CAS number: 77-86-1) to achieve concentrations of 1.22 mg/ml and 0.03 mg/ml, respectively. The reagents were mixed by vortexing to ensure dissolution, and aggregates formed after the sample was allowed to equilibrate for one hour.

Additional samples were prepared under comparable conditions with the addition of 0.1 M NaCl (Sigma Aldrich, CAS number 7647-14-5) to facilitate complexation and thus to promote aggregation.

The standard Stoichiometric Mixture of Colloidal Spheres sample is a mixture of four populations of monodisperse colloidal spheres in which each population has a distinct mean size and composition. The monodisperse spheres were purchased from Bangs Laboratories as aqueous dispersions at 10% solids. Stock suspensions were diluted one-thousand-fold with deionized water and then were combined in equal volumes to create a heterogeneous mixture. The four populations in this mixture are polystyrene spheres of diameter $2a_p = 0.71 \pm 0.09$ μm (Catalog Code PS03N, Lot Number 9402) and $2a_p = 1.58 \pm 0.14$ μm (Catalog Code PS04N, Lot Number 9258), and silica spheres of diameter $2a_p = 0.69 \pm 0.07$ μm (Catalog Code SS03N, Lot Number 8933) and $2a_p = 1.54 \pm 0.16$ μm (Catalog Code SS04N, Lot Number 5305). The quoted range of particle size is estimated by the manufacturer using dynamic light scattering for the smaller spheres, and by the Coulter principle for the larger spheres.

Silicone spheres composed of polydimethylsiloxane (PDMS) were synthesized by base catalyzed hydrolysis and copolymerization of difunctional diethoxydimethyl-silane (DEDMS) (Sigma-Aldrich, CAS number 78-62-6, 3 vol %) and trifunctional triethoxymethylsilane (TEMS) (Sigma-Aldrich, CAS number 2031-67-6, 2 vol %) following a standard protocol [Obey et al. J. Colloid Interface Sci. 1994, 163:454-463; Goller et al. Colloids Surfaces, 1997; 123-124:183-193.] A mixture of DEDMS and TEMS with 60:40 stoichiometry is added into deionized water (Millipore MilliQ, 93 vol %) at (28-30) wt % and ammonium hydroxide solution (ACROS Organics 2 vol %) to obtain a total volume of 10 ml. The sample was shaken vigorously with a vortexer for 4 min at room temperature to initiate nucleation, and then left to polymerize on a rotating frame at 10 rpm for three hours. Fully grown silicone spheres were then mixed with suspensions of protein aggregates at a volume fraction of $10^{-4}$ to obtain an effective concentration of spheres of $4 \times 10^6$/ml.

These polymerized spheres share most properties with unpolymerized silicone oil droplets. Their mean refractive index, $1.388 \pm 0.002$, exceeds that of DEDMS, 1.381, and TEMS, 1.383, as determined with an Abbe refractometer (Edmund Optics) and by holographic characterization.

Verification of Precision and Accuracy

Figure 3A:
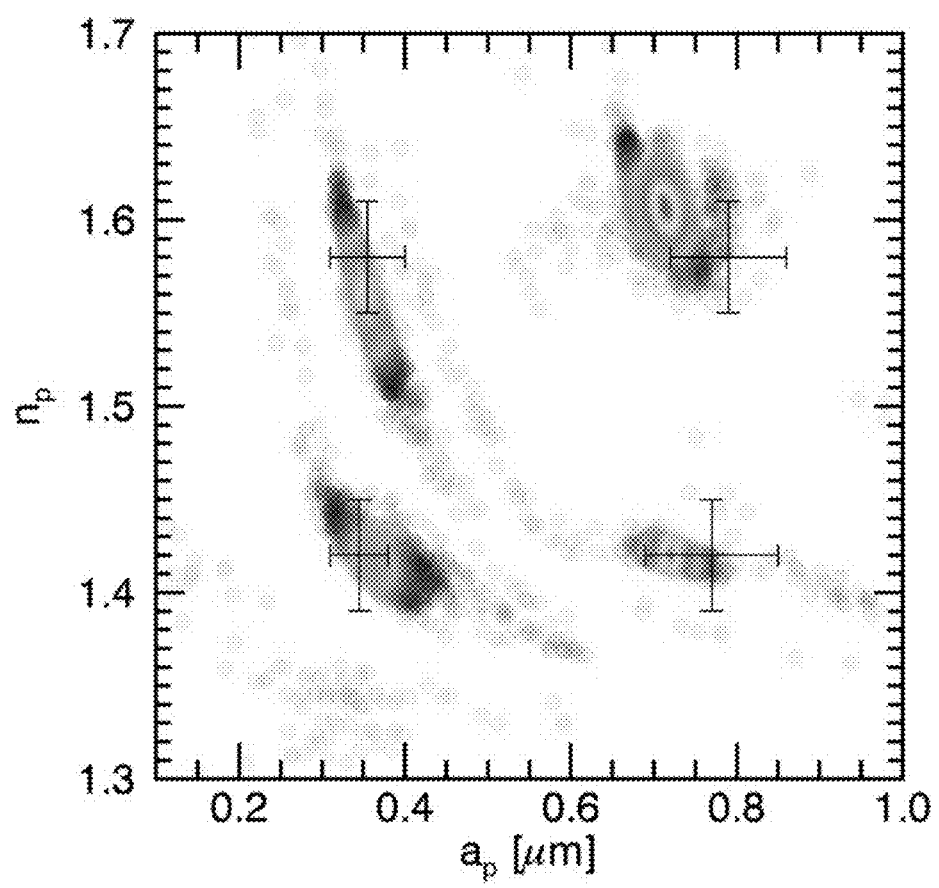
FIG. 3A is a scatter plot of radius $a_p$ and refractive index $n_p$ obtained with holographic characterization of a heterogeneous colloidal dispersion composed of a mixture of four different types of particles. Results for 20,000 particles are plotted. Superimposed crosses indicate the manufacturer's specification for each of the four populations. These results establish holographic characterization's ability to differentiate particles by composition as well as by size.
Figure 3B:
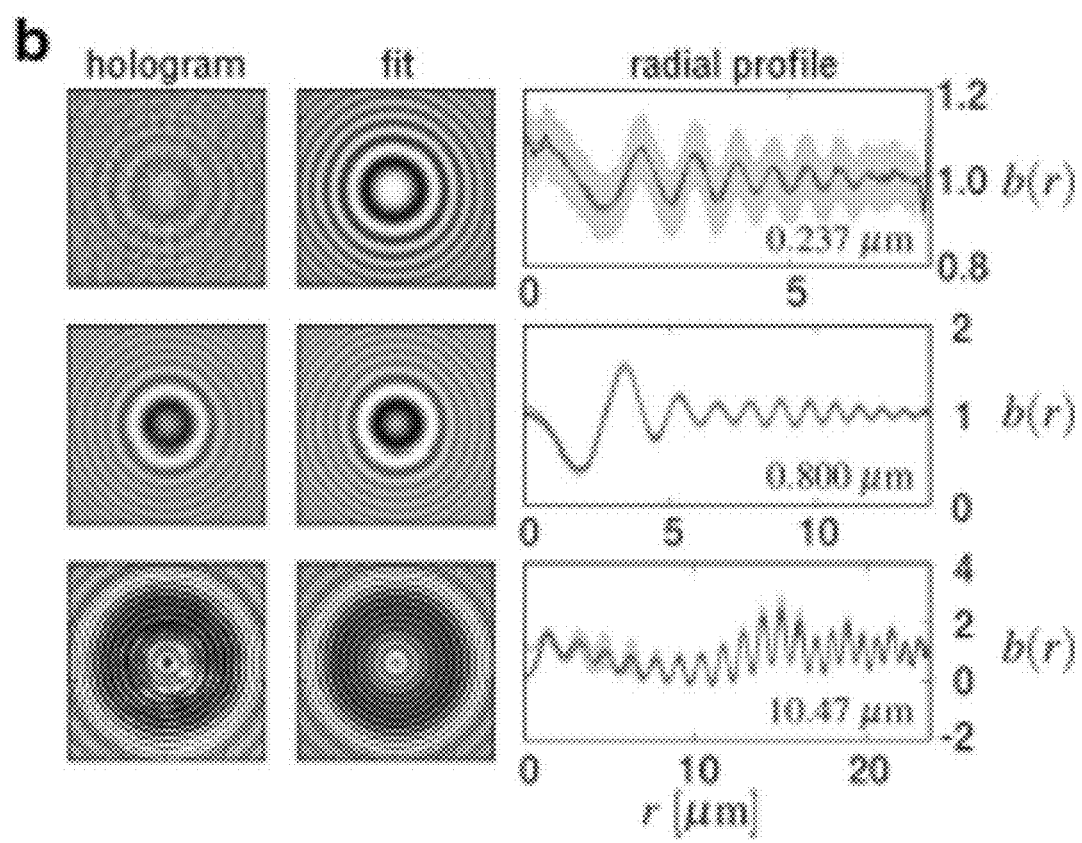
FIG. 3B shows measured holograms of colloidal polystyrene spheres in water together with fits, demonstrating the range of particle sizes amenable to holographic characterization. These typical examples were obtained for spheres with radii $a_p=0.237$ mm (224 pixel×224 pixel region of interest), 0.800 mm (356 pixel×356 pixel), and 10.47 mm (608 pixel×608 pixel). The fit to each hologram yields values for the particle's radius, $a_p$, and refractive index, $n_p$. Radial profiles, b(r), are obtained from these holograms and their fits by averaging the normalized intensity over angles around the center of each feature, and are plotted as a function of distance r from the center of the feature. Experimental data are plotted as darker (blue) curves within shaded regions representing the measurement's uncertainty at that radius. Fits are superimposed as lighter (orange) curves and closely track the experimental data.

The data in FIG. 3 were obtained by holographic characterization of a model colloidal dispersion consisting of a stoichiometric mixture of four distinct types of monodisperse colloidal spheres. Each of the four peaks in FIG. 3A represents the properties of one of those populations. In each case, the holographically measured distribution of properties is consistent with the manufacturer's specification. This agreement, together with complementary tests in previous publications, establishes the precision and accuracy of particle-resolved holographic characterization.

This data set also illustrates the unique ability of holographic characterization to characterize heterogeneous colloidal dispersions. Other techniques could have resolved the size distribution of any of the monodisperse colloidal components individually. No other technique, however, could have resolved the four populations in this mixture.

FIGS. 4A-4D offer an experimental demonstration of the range of particle sizes over which holographic characterization yields useful results. The 3 holograms presented here were recorded for 3 different polystyrene spheres dispersed in water, one with a radius of $a_p$ ¼ 0.237 mm, at the small end of the technique's effective range, one with a radius of $a_p$ ¼ 0.800 mm, and the third with a radius of $a_p$ ¼ 10.47 mm. These measured holograms (FIG. 4A) are presented alongside corresponding pixel-by-pixel fits (FIG. 4B) to the predictions of the theory of light scattering, which are parameterized by each particle's 3-dimensional position, radius, and refractive index. The quality of a fit can be assessed by plotting the radial profile (FIG. 4C) of the normalized image intensity, b(r). This is obtained by averaging the 2-dimensional intensity pattern over angles around the center of the scattering pattern. Curves obtained from the measured data are plotted in FIG. 4D within shaded regions that represent measurement uncertainties. Curves obtained from the fits are overlaid on the experimental data for comparison. The fits track the experimental data extremely well over the entire range of particle sizes.

Characterization of Subvisible Insulin Aggregates

Although the bovine insulin sample appeared clear under visual inspection, the data in FIG. 2 reveal a concentration of $(3.9 \pm 0.5) \times 10^7$ subvisible bovine insulin aggregates per milliliter, which corresponds to a volume fraction of roughly 10-3. Uncertainty in this value results from feature identification errors for the largest particles and uncertainty in the flow speed. Aggregates with radii smaller than 200 nm are not detected by the holographic characterization system and therefore were not counted in these totals. The distribution of particle characteristics is peaked at a radius of 1.6 μm, and is both broad and multimodal. No aggregates were recorded with radii exceeding 4.2 μm, which suggests that such large-scale aggregates are present at concentrations below $10^4$/ml.

The aggregates' refractive indexes vary over a wide range from just above that of the buffer, nm=1.335, to slightly more than 1.42. This range is significantly smaller than the value around 1.54 that would be expected for fully dense protein crystals. This observed upper limit is consistent, however, with recent index-matching measurements of the refractive index of protein aggregates. These latter measurements were performed by perfusing protein aggregates with index-matching fluid, and therefore yield an estimate for the refractive index of the protein itself. Holographic characterization, by contrast, analyzes an effective scatterer comprised of both the higher-index protein and also the lower-index buffer that fills out the sphere. It has been shown that such an effective sphere has an effective refractive index intermediate between that of the two media in a ratio that depends on the actual particle's porosity. More porous or open structures have smaller effective refractive indexes. The influence of porosity on the effective refractive index, furthermore, is found to be proportionally larger for particles with larger radii.

The effective sphere model account for general trends in the holographic characterization data under the assumption that the protein aggregates have open irregular structures. This proposal is consistent with previous ex situ studies that have demonstrated that bovine insulin forms filamentary aggregates.

The particular ability of holographic characterization to record both the size and the refractive index of individual colloidal particles therefore offers insights into protein aggregates' morphology in situ and without dilution and without any other special preparation. This capability also enables holographic characterization to distinguish protein aggregates from common contaminants such as silicone oil droplets and rubber particles, which pose problems for other analytical techniques.

Characterization of Subvisible BSA Aggregates

FIG. 5 shows comparable holographic characterization results for the two samples of bovine serum albumin. The data in FIG. 5A were obtained for the sample prepared without additional salt. As for the insulin sample, holographic characterization of the BSA sample reveals $\pm 0.5 \times 10^6$ aggregates/ml in the range of radii running from 300 nm to 2.5 μm, and a peak radius of 0.5 μm. No aggregates were observed with radii exceeding 2.8 μm, which suggests that larger aggregates are present at concentrations below $10^4$/ml.

The upper panel in FIG. 5A is a projection of the joint distribution, $p(a_p, n_p)$, into the distribution of aggregate sizes, $p(a_p)$. This projection more closely resembles results provided by other size-measurement techniques, such as dynamic light scattering. Although the observed concentration of subvisible protein aggregates is below the detection threshold for DLS, DLS measurements reveal a concentration of roughly $10^9$ aggregates/ml whose radii are smaller than 100 nm, and thus are too small for holographic characterization. As for the BI samples, the anticorrelation between $a_p$ and $n_p$ evident in FIGS. 5A-5F suggests that BSA-PAH complexes have an open structure. This is consistent with previous ex situ studies that demonstrate that BSA aggregates into weakly branched structures.

Adding salt enhances complexation and increases the mean aggregate size by nearly a factor of two, and also substantially broadens the distribution of aggregate sizes, These trends can be seen in FIG. 5B. FIGS. 5A-5F also include projections of the relative probability densities, $p(a_p)$, that emphasize how aggregates' size distribution changes with growth conditions. What these projections omit is the striking change in the joint distribution of aggregate radii and refractive indexes from FIG. 5A to FIG. 5B. This shift suggests that the larger aggregates grown in the presence of added salt are substantially more porous. This insight into the aggregates' morphology would not be offered by the size distributions alone.

Role of Aggregate Morphology

Microflow Imaging

FIGS. 4A-4D present direct comparisons between holographic characterization and MFI for a representative sample of 6 BSA-PAH complexes whose morphologies range from nearly spherical compact clusters to extended spindly structures. Each aggregate's hologram is compared with a nonlinear least-squares fit to the predictions of Lorenz-Mie theory. The reduced $X^2$ statistic for these fits is used to arrange the results from best fits at the top to worst fits at the bottom. Each of the measured holograms also is used to reconstruct a volumetric image of the individual aggregate through Rayleigh-Sommerfeld deconvolution microscopy. The size of the reconstructed cluster then can be compared with the effective radius obtained from holographic characterization.

Even the two most compact clusters in FIG. 4A appear to be substantially aspherical. Their holograms, nevertheless, are very well reproduced by the nonlinear fits. The $X^2$ metrics for these fits are close to unity, suggesting that the model adequately describes the light-scattering process and that the single-pixel noise is well estimated. Values for the aggregate radius are consistent with the size estimated from Rayleigh-Sommerfeld reconstruction. Circles with the holographically determined radii are superimposed on the numerically refocused bright-field images in FIG. 4D for comparison. This success is consistent with previous comparisons of Lorenz-Mie and Rayleigh-Sommerfeld analyses for colloidal spheres and colloidal rods.

Errors increase as aggregates become increasingly highly structured and asymmetric. Even so, estimates for the characteristic size are in reasonable agreement with the apparent size of the bright-field reconstructions even for the worst case. This robustness arises because the effective size of the scatterer strongly influences the size and contrast of the central scattering peak and the immediately surrounding intensity minimum. Faithful fits in this region of the interference pattern therefore yield reasonable values for the scatterer's size. The overall contrast of the pattern as a whole encodes the scatterer's refractive index, and, thus, is very low for such open-structured clusters.

These representative examples are consistent with earlier demonstrations that holographic characterization yields useful characterization data for imperfect spheres and aspherical particles. Particularly for larger aggregates, the estimated value for the refractive index describes an effective sphere. The estimated radius, however, is a reasonably robust metric for the aggregate's size.

Independent of the ability of holographic characterization to provide insight into morphology, these results demonstrate that holographic microscopy usefully detects and counts subvisible protein aggregates in solution. These detections by themselves provide information that is useful for characterizing the state of aggregation of the protein solution in situ without requiring extensive sample preparation. Holographic microscopy's large effective depth of field then serves to increase the analysis rate relative to conventional particle imaging analysis.

Figure 8A:
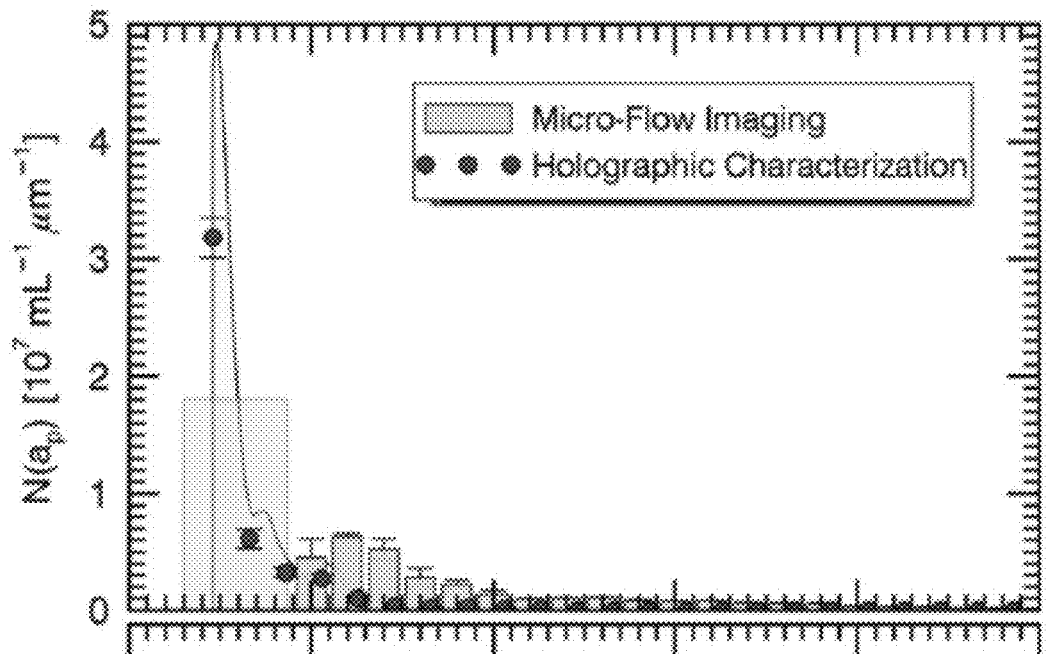
FIGS. 8A-8B show a comparison of size distributions measured with microflow imaging and holographic characterization. Each bin represents the number of particles per milliliter of solution in a range of ±100 nm about the bin's central radius.
Figure 8B:
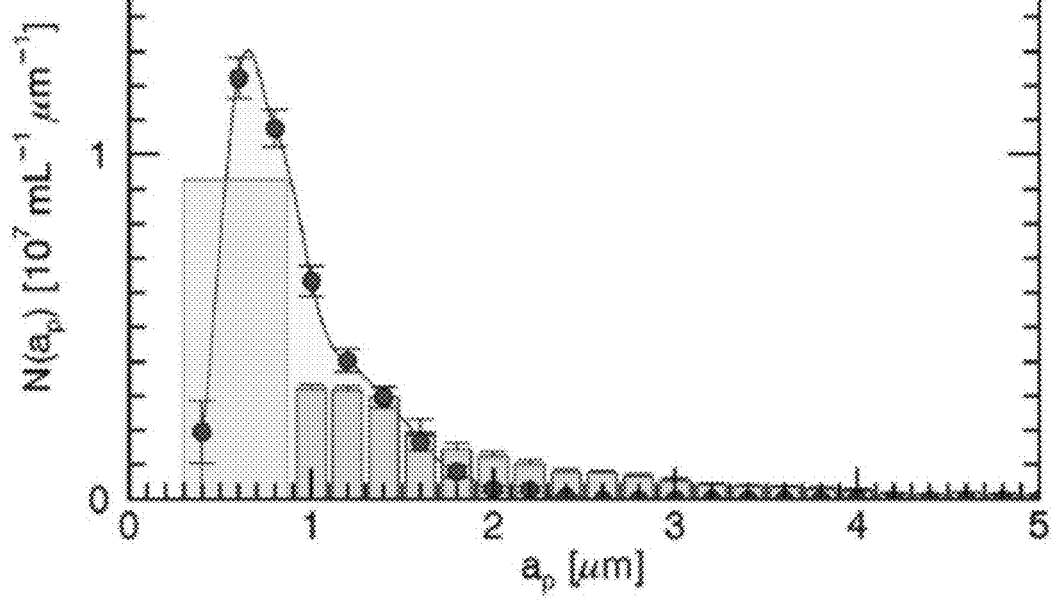

Like holographic characterization, MFI yields particle-resolved radius measurements that can be used to calculate the concentration of particles in specified size bins. These results may be compared directly with projected size distributions produced by holographic characterization. The data in FIGS. 8A-8B show such a comparison for the BSA-PAH complexes with and without added salt featured in FIG. 5C-5D. Results are presented as the number, $N(a_p)$, of aggregates per milliliter in a size range of ±100 nm around the center of each bin in $a_p$. The holographic characterization data from FIGS. 5B and 5D are rescaled in this plot for comparison. Independent studies demonstrate that MFI analysis yields reliable size estimates for aggregates with radii larger than 1 nm. Diffraction causes substantial measurement errors for smaller particles. We, therefore, collect MFI results for smaller particles into 600-nm wide bins in FIGS. 8A and 8B, with corresponding normalization. The lower end of this bin's range corresponds with the smallest radii reported by holographic characterization. Agreement between holographic characterization and MFI is reasonably good over the entire range of particle sizes plotted. Both techniques yield consistent values for the overall concentration of $10^7$ aggregates/mL. MFI systematically reports larger numbers of aggregates on the large end of the size range and fewer on the small end. This difference can be attributed to the most elongated and irregular aggregates, such as the last example in FIGS. 4A-4D, whose size is underestimated by holographic characterization. This effect of morphology on holographic size characterization has been discussed previously. Even in these cases, holographic characterization correctly detects the particles' presence and identifies them as micrometer-scale objects. Both MFI and holographic characterization yield consistent results for the total number density of aggregates.

For particles on the smaller end of the size range, MFI provides particle counts but no useful characterization data. Holographic characterization, by contrast, offers reliable size estimates in this regime. Over the entire range of sizes considered, holographic characterization also provides estimates for particles' refractive indexes.

Dynamic Light Scattering

To verify the presence of subvisible protein aggregates in our samples, we also performed DLS measurements. Whereas holographic characterization and MFI yield particle-resolved measurements, DLS is a bulk characterization technique. Values reported by DLS reflect the percentage, $P(a_h)$, of scattered light that may be attributed to objects of a given hydrodynamic radius, an. The resulting size distribution therefore is weighted by the objects' light-scattering characteristics. Scattering intensities can be translated at least approximately into particle concentrations if the particles are smaller than the wavelength of light and if they all have the same refractive index. Direct comparisons are not possible when particles' refractive indexes vary with size, as is the case for protein aggregates. In such cases, DLS is useful for confirming the presence of scatterers within a range of sizes. FIG. 6 presents DLS data for the same samples of BSA-PAH complexes presented in FIG. 3. For both samples, DLS reveals the presence of an abundance of scatterers with radii smaller than 100 nm. The detection threshold of DLS for scatterers of this size is roughly $10^8$ aggregates/mL, as determined by independent studies. We conclude that both samples have at least this concentration of submicrometer-diameter aggregates. Such objects are smaller than the detection limit for our implementation of holographic video microscopy and so were not resolved in FIG. 3.

The distribution shifts to larger sizes in the sample with added salt, consistent with the results of holographic characterization. Both samples show a very small signal, indicated by an arrow in FIG. 9, for subvisible objects whose hydrodynamic radius is 2.8 nm. This confirms the presence of such scatterers in our sample at a concentration just barely above the detection threshold of DLS for objects of that size.

The sample with added salt also has a clear peak around $a_h$=400±20 nm that is in the detection range of holographic characterization. The corresponding peak in FIG. 5C appears at a substantially larger radius, $a_p$=770±20 nm. One likely source of this discrepancy is that holographic characterization reports the radius of an effective bounding sphere, whereas DLS reports the hydrodynamic radius, which can be substantially smaller for open structures. Another contributing factor is that larger aggregates have lower effective refractive indexes and thus scatter light proportionately less strongly than smaller aggregates. This effect also shifts the apparent size distribution downward in DLS measurements. It does not, however, affect holographic characterization, which reports both the size and refractive index of each object independently.

Holographic Differentiation of Silicone Spheres from Protein Aggregates

DLS cannot distinguish protein aggregates from other populations of particles in suspension. MFI can differentiate some such contaminants by morphology: silicone droplets, for example, tend to be spherical, whereas protein aggregates tend to have irregular shapes. Morphological differentiation works best for particles that are substantially larger than the wavelength of light, whose structural features are not obscured by diffraction. Through the information it provides on individual particles' refractive indexes, holographic characterization offers an additional avenue for distinguishing micrometer-scale objects by composition. We demonstrate this capability by performing holographic characterization measurements on BSA samples that are deliberately adulterated with silicone spheres.

Holographic Characterization of Silicone Spheres

Figure 10A:
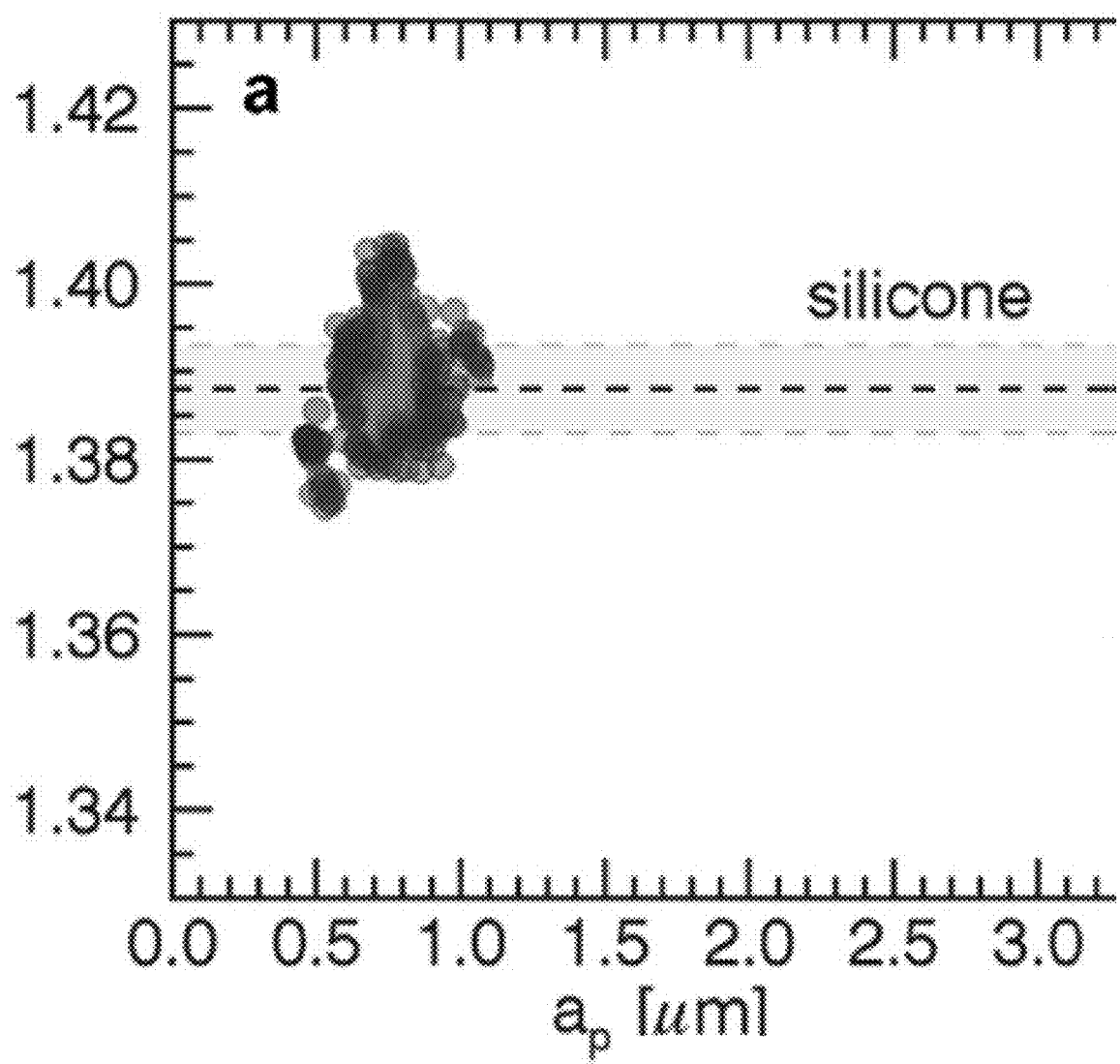
FIGS. 10A and 10B show holographic characterization data for silicone spheres dispersed in deionized water. The gray-shaded region denotes the range of refractive indexes expected for these particles based on their composition.
Figure 10B:
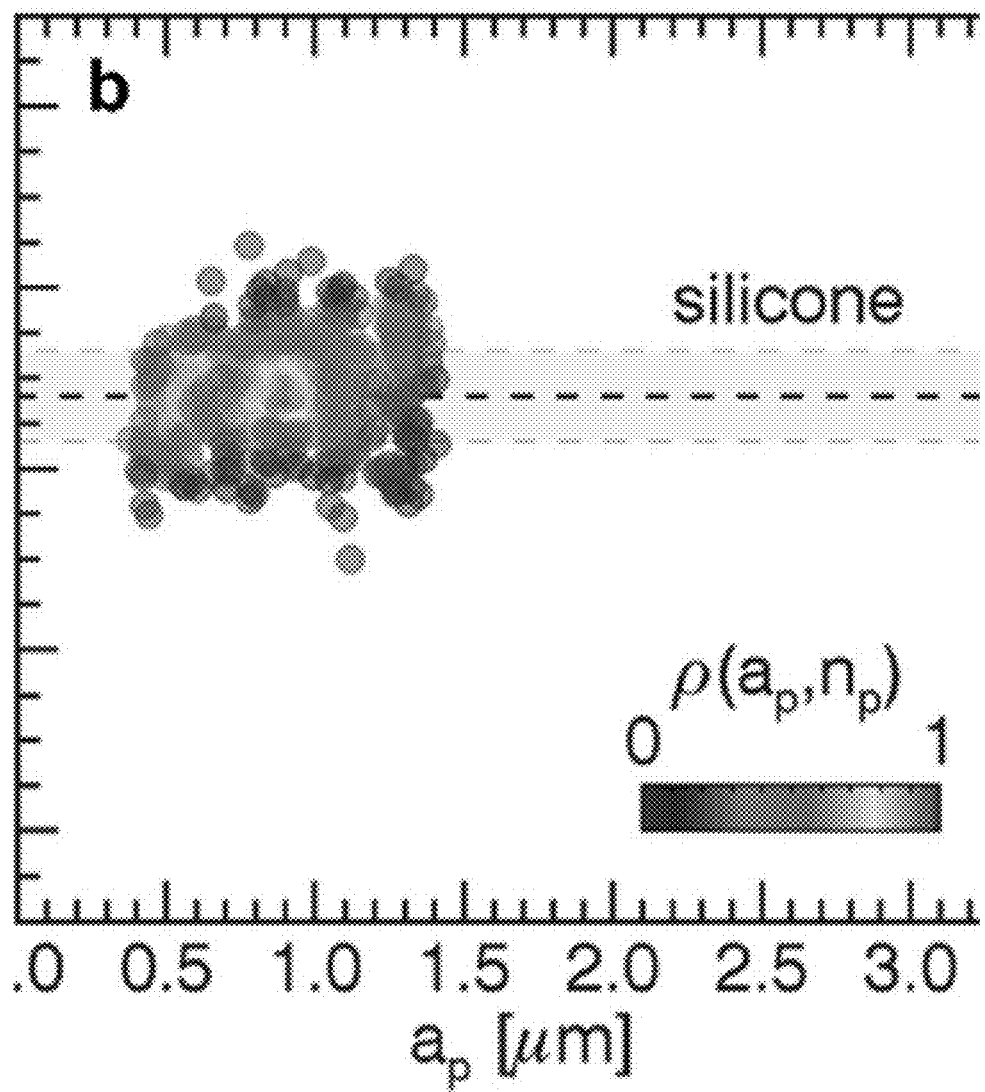

FIGS. 10A-10B show holographic characterization data for silicone spheres dispersed in deionized water. The sample in FIG. 10A is comparatively monodisperse with a sample-averaged radius of 0.75±0.09 nm. The particles in FIG. 10B are drawn from a broader distribution of sizes, with a mean radius of 0.87±0.28 nm. Both samples of spheres have refractive indexes consistent with previously reported values for polydimethylsiloxane with 40% cross-linking, $n_p=1.388\pm0.005$. This range is indicated with a shaded region in FIGS. 10A-10B.

Unlike the protein aggregates, these particles' refractive indexes are uncorrelated with their sizes. This is most easily seen in the polydisperse sample in FIG. 10B and is consistent with the droplets having uniform density and no porosity. We expect to see the same distribution of single-particle properties when these silicone spheres are codispersed with protein aggregates.

Differential Detection of Silicone Spheres

Figures 11A, 11B:
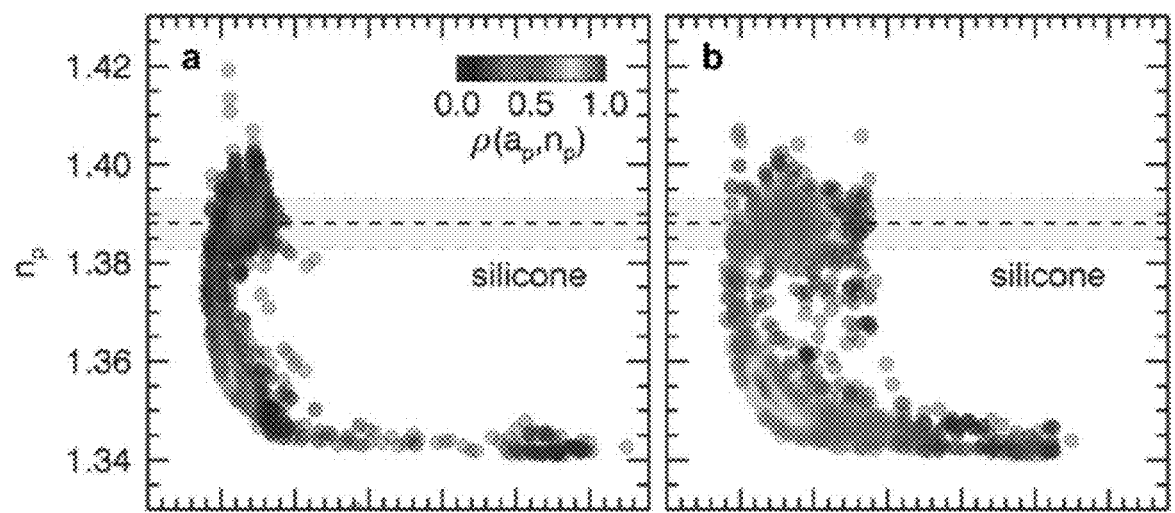
FIGS. 11A-11D show holographic measurement of the relative probability density, $r(a_p, n_p)$, of particle radius and refractive index for suspensions BSA-PAH complexes spiked with added silicone spheres.
Figures 11C, 11D:
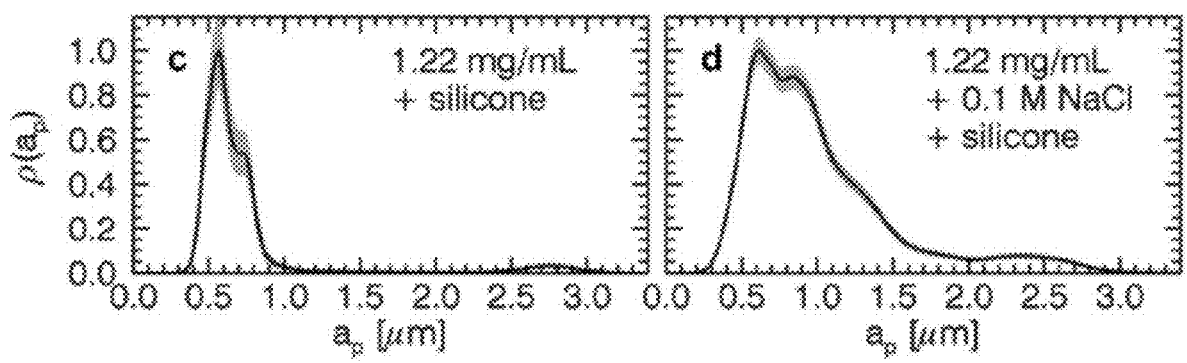

The data in FIG. 11A were obtained from a sample of BSA prepared under the same conditions as FIG. 5A but with the addition of monodisperse silicone spheres at a concentration of 4×106 particles/mL. The resulting distribution of particle properties is clearly bimodal with one population resembling that obtained from protein aggregates alone and the other having a refractive index consistent with that of the silicone spheres, $n_p=1.388\pm0.005$. The sample in FIG. 11B similarly were prepared under conditions comparable to those from FIG. 5C with the addition of polydisperse silicone spheres from the sample in FIG. 10B. Consistency between features associated with protein aggregates in FIGS. 5A-5D and FIGS. 11A-11B demonstrate that both the sample preparation protocol and also the holographic characterization technique yield reproducible results from sample to sample, and that holographic characterization of protein aggregates is not influenced by the presence of extraneous impurity particles.

Figure 9:
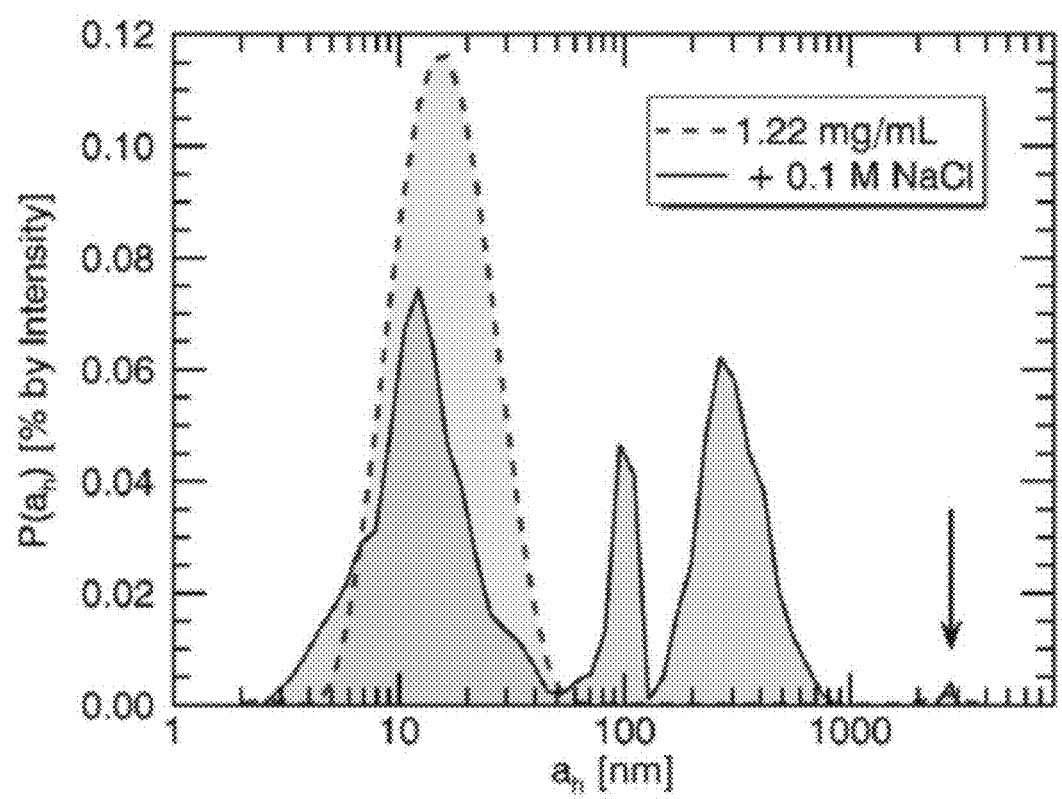
FIG. 9 shows a characterization of BSA-PAH complexes by dynamic light scattering (DLS). Values represent the percentage, $P(a_h)$, of the scattered light's intensity due to scatterers of a given hydrodynamic radius, ah. The arrow indicates a small peak in both distributions around ah ¼ 2.8 mm.

Interestingly, both distributions feature a small peak around $a_p=2.8$ nm that corresponds to the peak in the DLS data from FIG. 9. This feature is not present in FIGS. 3A-3F. It is likely that this very small population of larger aggregates was present in those samples but at a concentration just below the threshold for detection in a 10-min measurement.

The distributions of features associated with silicone droplets in FIGS. 11A-11B also agree well with the holographic characterization data on the droplets alone from FIGS. 10A-10B. These results demonstrate that the refractive-index data from holographic characterization can be useful for distinguishing protein aggregates from silicone oil droplets. Such differentiation would not be possible on the basis of the size distribution alone, as can be seen from the projected data in FIGS. 11A-11D.

Holographic characterization cannot differentiate silicone droplets from protein clusters whose refractive index is the same as silicone's. Such ambiguity arises for the smallest particles analyzed in FIGS. 11A-11D. Spherical silicone droplets sometimes can be distinguished from irregularly shaped protein aggregates under these conditions using morphological data obtained through deconvolution analysis of the same holograms. The distinction in these cases still would be less clear than can be obtained with Resonant Mass Measurement (RMM), which differentiates silicone from protein by the sign of their relative buoyancies. In cases where specific particles cannot be differentiated unambiguously, the presence of silicone droplets still can be inferred from holographic characterization data because such particles create a cluster in the $(a_p, n_p)$ plane whose refractive index is independent of size. The relative abundances of the two populations then can be inferred, for example, by statistical clustering methods.

Discussion of Example Results

As an optical probe of protein aggregate properties, holographic characterization is orthogonal to such non-optical techniques as the Coulter principle or Resonant Mass Measurement (RMM). As an imaging technique, it is related to Micro-Flow Imaging (MFI) and Nanoparticle Tracking Analysis (NTA). Holographic characterization benefits, however, from its large effective depth of field and its ability to monitor refractive index as well as size. Because MFI and holographic characterization can analyze a single particle with a single snapshot, both are inherently faster than NTA, which relies on time-series analysis.

Holographic characterization also is related to light-scattering techniques such as dynamic light scattering (DLS) and light obscuration (LO). It offers greater counting sensitivity for micrometer-scale objects than dynamic light scattering, and access to smaller particles than light obscuration, without requiring dilution. Unlike other scattering techniques, holographic characterization does not require the particles' refractive indexes as inputs, but rather provides the refractive index as an output.

Comparisons among these techniques are summarized in Table I, which is a comparison of high-throughput characterization techniques for subvisible protein aggregates. The size range refers to the radius of the effective sphere detected by each method. The fourth column indicates whether the technique is capable of measuring aggregate morphology. References describe independent assessments of techniques' capabilities for characterizing protein aggregates.

TABLE I

| Method | Size [μm] | Number/ml | Morphology | Comments |
|---|---|---|---|---|
| Holographic Characterization | 0.3-10 | $10^4$-$10^8$ | Yes | Measures both size and refractive index. Does not require calibration standards. Differentiates by size and composition. |
| Dynamic Light Scattering (DLS) | 0.001-1 | $10^8$-$10^{10}$ | No | Sample-averaged measurement. No differentiation. |
| Electric Sensing Zone (ESZ) Coulter Principle | 0.1-1600 | 1-$10^5$ | No | Requires compatible electrolyte. Typically requires sample dilution. Requires calibration with size standards. Size range determined by orifice selection. No differentiation. |
| Light Obscuration (LO) | 1-200 | $10^3$-$10^5$ | No | Typically requires sample dilution. Sensitive to refractive index variations. Requires calibration with size standards. No differentiation. |
| Dynamic Imaging Analysis (DIA) Micro-Flow Imaging (MFI) | 1-400 | $10^4$-$10^6$ | Yes | Differentiation based on morphology rather than composition. |
| Nanoparticle Tracking Analysis (NTA) | 0.03-1 | $10^7$-$10^9$ | No | Measurement time increases with particle radius. No differentiation. |
| Resonant Mass Measurement (RMM) Archimedes | 0.3-4 | $10^6$-$10^9$ | No | Particle size estimated indirectly from mass. Differentiates between positively and negatively buoyant particles. |

The measurements presented here demonstrate that holographic video microscopy together with Lorenz-Mie analysis can detect, count and characterize subvisible protein aggregates. Data acquisition is rapid, typically taking no more than 15 min, and requires no special sample preparation. One implementation is effective for aggregates ranging in radius from 300 nm to 10 μm and at concentrations from $10^4$ aggregates/ml to $10^8$ aggregates/ml. The same holograms used for characterization measurements also can be interpreted to estimate the morphology of individual protein aggregates through numerical back-propagation. Calibration is straightforward, requiring only the laser wavelength, the microscope's magnification and the medium's refractive index. It is believe that such holographic characterization of protein aggregates will be useful for assessing the stability of biopharmaceutical formulations, for process control during manufacturing, and for quality assurance both at the point of sale, and also potentially at the point of use.

Anticorrelation Between Aggregate Size and Refractive Index

As noted above, there is an observed strong anticorrelation between aggregate size and refractive index revealed in FIGS. 5A, 5C, and 5E. Such would not have been detected by any prior art particle-characterization technique. The values for the single-particle refractive index, moreover, are substantially smaller than the value of roughly 1.45 that would be expected for proteins at the imaging wavelength. Indeed, the estimated refractive index for the largest particles is not much larger than that of water, 1.335.

Anticorrelation between size and refractive index together with low values for refractive index have been identified as hallmarks of particle porosity. Rather than being homogeneously porous, however, it is believed that protein aggregates will have the fractal structure that arises naturally through growth by aggregation.

To test this idea, a protein aggregate was modeled as a fractal cluster of fractal dimension D. The fractal model was selected for its known relation to the geometry of random aggregates and for simplicity due to reliance on a single parameter, fractal dimension D, for predicting density. One of skill in the art will appreciate that other appropriate models can be used to predict properties of the protein aggregate, including density. The volume fraction of proteins of radius $a_0$ within an aggregate of radius $a_p$ therefore is $$\phi(a_p) = \left(\frac{a_0}{a_p}\right)^{3-D}. \tag{1}$$

This proportion of the cluster is composed of a material with refractive index $n_0$. The remainder of the volume presumably is filled with the fluid medium, which has a lower refractive index, $n_m$. The apparent refractive index, $n_p$ of the particle as a whole is given by effective medium theory $$f(n_p) = f(n_0) + (1-\phi)f(n_m), \tag{2}$$

where the Lorenz-Lorentz factor is $$f(n) = \frac{n^2 - 1}{n^2 + 2}. \tag{3}$$

From this, $$\ln\left(\frac{f(n_p) - f(n_m)}{f(n_0) - f(n_m)}\right) = (3 - D)\ln\left(\frac{a_0}{a_p}\right). \tag{4}$$

Even if $n_0$ and $a_0$ are not known independently, this scaling relation provides a means to characterize the morphology of a population of aggregates by estimating the ensemble-averaged fractal dimension.

Figure 6A:
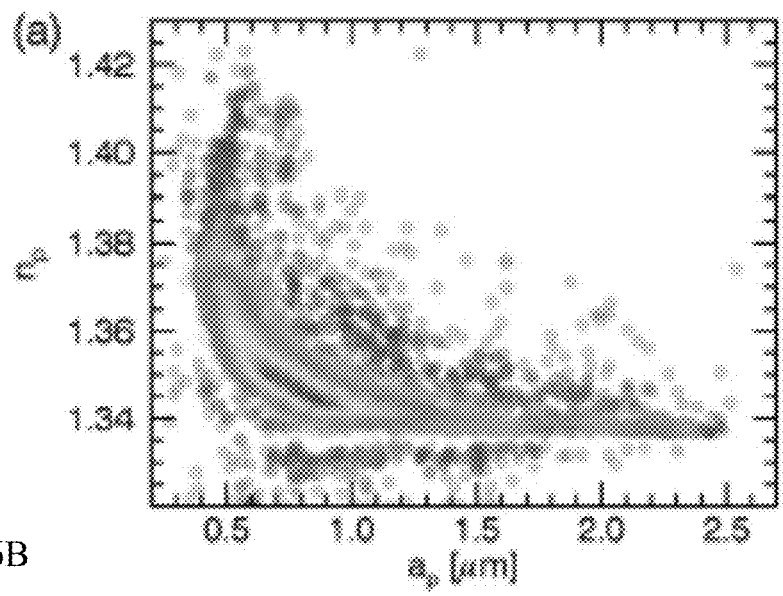
FIG. 6A shows combined data for all three BSA samples.
Figure 6B:
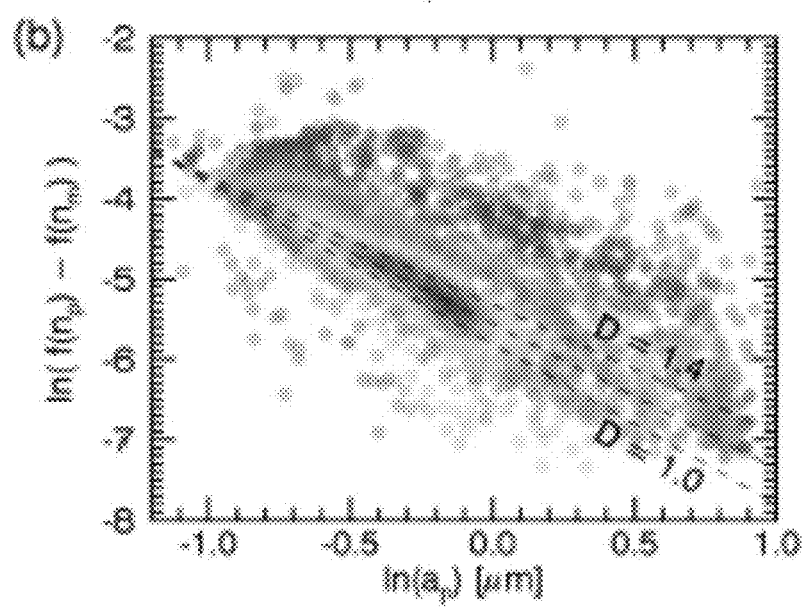
FIG. 6B shows data rescaled according to Equation 4.

The data in FIGS. 6A-6B show the results of such an analysis. FIG. 6A compiles all of the data from FIGS. 5A, 5C, and 5E under the assumption that the same morphology would arise under all three sets of growth conditions. This assumption is borne out in FIG. 6B which shows the same data plotted according to the scaling relation in Eq. (4). In particular, the linear trend in FIG. 6B supports the assumptions underlying Eq. (4), including the assumption that the three populations of aggregates have consistent growth habits.

Dashed lines superimposed on the data in FIG. 6B indicate slopes consistent with D=1, 1.2 and 1.4, with best agreement being obtained for D=1.2. This result suggests that the BSA aggregates are filamentary, with few branches. The fractal model may be used for dense blobs (D=3), linear chains (D=1) as well as structures in between (typically D>3>1). The holograms' apparent spherical symmetry therefore suggests that the aggregates are composed of clusters of filaments. This is consistent with electron microscopy studies of BSA aggregation under comparable conditions. Estimating the fractal dimension through holographic characterization improves upon electron microscopy because it can be performed in situ and does not entail any of the structural transformations inherent in sample preparation. Holographic characterization also offers advantages over conventional light scattering because it does not require estimates for the monomer refractive index. All of the calibration data required for the measurement is available from single-particle characterization data and the overall calibration of the instrument.

The success of this scaling analysis provides additional evidence that the holographically estimated values for the radius and refractive index of individual protein aggregates accurately reflects the aggregates' actual properties. This result is not unreasonable given the observed symmetry of single-aggregate holograms, such as the example in FIG. 1A, and their amenability to fitting with the Lorenz-Mie result for ideal spheres. These observations then suggest that holographic characterization can be effective for analyzing the properties of individual protein aggregates and therefore for assessing the properties of dispersions of protein aggregates. Beyond providing information on the size distribution of protein aggregates, holographic characterization also offers insights into composition and morphology through the refractive index.

The information provided by holographic characterization should provide useful feedback for formulating protein dispersions, particularly in applications where the size of aggregates must be monitored and limited. Real-time implementations of holographic characterization similarly should be useful for process control and quality assurance in such applications.

Differentiation

FIGS. 5A, 5C, and 5E illustrate the ability, in one embodiment, of systems and methods described herein to provide differentiation. In this context, "differentiation" is the ability to distinguish a desired material, such as protein aggregates, from other materials in a suspension. The refractive index data provided by holographic characterization can be used to distinguish protein aggregates from contaminants such as silicone droplets. This is important because contaminants, including silicone droplets and rubber particles, often find their way into protein solutions and can be mistaken for protein aggregates by other characterization techniques. Such misidentification can suggest that there is a problem with the product, when no problem exists, or fail to identify a contaminated batch of product.

Figures 12A, 12B, 12C:
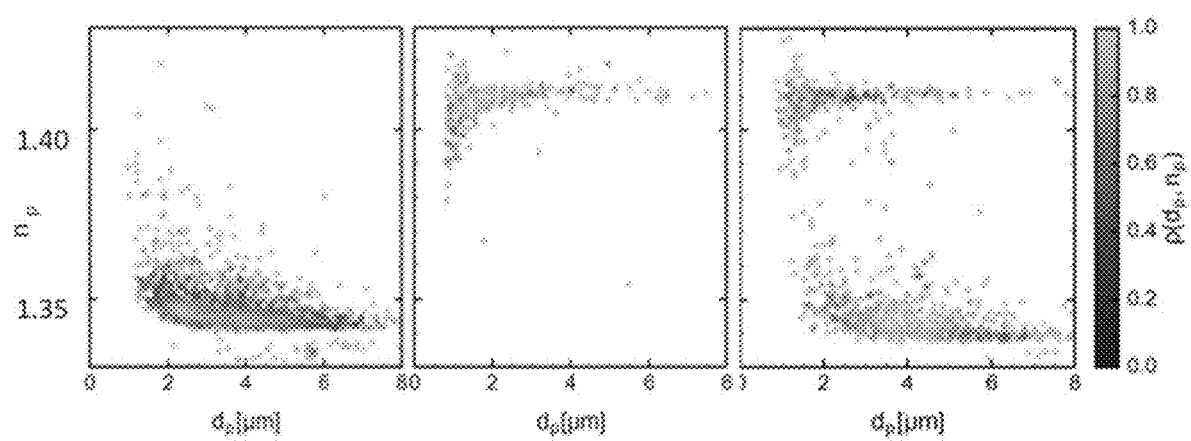
FIGS. 12A-12C illustrate results showing the distinguishing of protein and silicone oil separately.

Further, FIGS. 12A-12C illustrate human IgG, silicone oil and then the two combined in one sample. As can be seen, the protein aggregates (FIG. 12A) and the silicone oil (FIG. 12B) have very different signatures and are clearly distinguishable when they are in the same sample (FIG. 12C). The silicone oil signature is a textbook example holographic characterization of oil emulsions while the protein can be readily distinguished.

Using systems and methods described herein, one can differentiate objects by their refractive indexes, which is a unique capability. Thus, the differentiation is by the actual composition, to which the refractive index is directly related, rather than some other aspect such as morphology (which may be the same for different materials, thus given false results, either false positive or false negative). For example, one popular technique uses morphology to distinguish silicone from protein, under the assumption that silicone droplets are spherical and protein aggregates are not. However, this assumption fails in a number of important scenarios, including for small protein aggregates where the size is below the ability of the technique to differentiate them from spheres.

Computer Implementation

Figure 7:
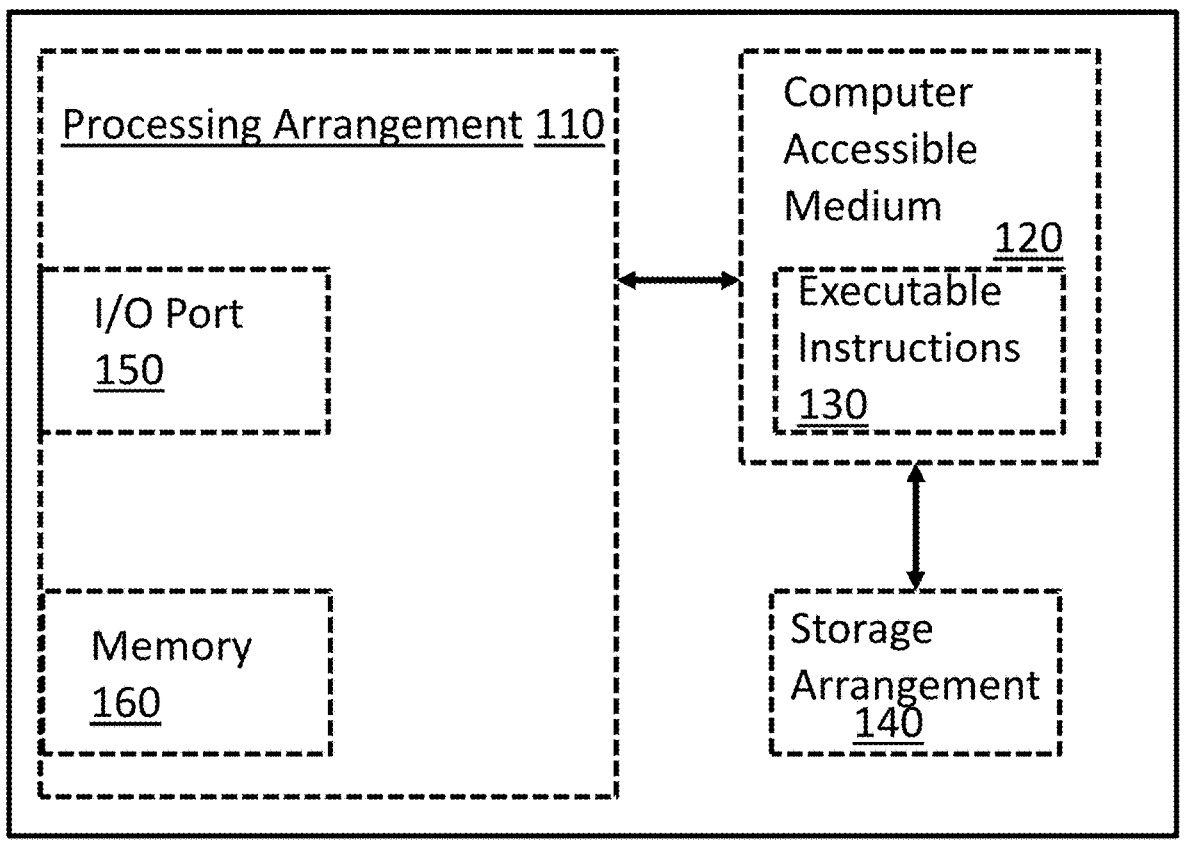
FIG. 7 illustrates a computer system for use with certain implementations.

As shown in FIG. 7, e.g., a computer-accessible medium 120 (e.g., as described herein, a storage device such as a hard disk, floppy disk, memory stick, CD-ROM, RAM, ROM, etc., or a collection thereof) can be provided (e.g., in communication with the processing arrangement 110). The computer-accessible medium 120 may be a non-transitory computer-accessible medium. The computer-accessible medium 120 can contain executable instructions 130 thereon. In addition or alternatively, a storage arrangement 140 can be provided separately from the computer-accessible medium 120, which can provide the instructions to the processing arrangement 110 so as to configure the processing arrangement to execute certain exemplary procedures, processes and methods, as described herein, for example. The instructions may include a plurality of sets of instructions. For example, in some implementations, the instructions may include instructions for applying radio frequency energy in a plurality of sequence blocks to a volume, where each of the sequence blocks includes at least a first stage. The instructions may further include instructions for repeating the first stage successively until magnetization at a beginning of each of the sequence blocks is stable, instructions for concatenating a plurality of imaging segments, which correspond to the plurality of sequence blocks, into a single continuous imaging segment, and instructions for encoding at least one relaxation parameter into the single continuous imaging segment.

System 100 may also include a display or output device, an input device such as a key-board, mouse, touch screen or other input device, and may be connected to additional systems via a logical network. Many of the embodiments described herein may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art can appreciate that such network computing environments can typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Various embodiments are described in the general context of method steps, which may be implemented in one embodiment by a program product including computer-executable instructions, such as program code, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps.

Software and web implementations of the present invention could be accomplished with standard programming techniques with rule based logic and other logic to accomplish the various database searching steps, correlation steps, comparison steps and decision steps. It should also be noted that the words "component" and "module," as used herein and in the claims, are intended to encompass implementations using one or more lines of software code, and/or hardware implementations, and/or equipment for receiving manual inputs.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. Therefore, the above embodiments should not be taken as limiting the scope of the invention.

What is claimed is:

1. A method of characterizing a sample of plurality of particles, comprising:
    flowing the sample in a medium through an observation volume of a holographic microscope;
    generating a first set of holograms based upon holographic video microscopy of a particle $P_n$ of a first cluster of the plurality of particles within the observation volume at a first time;
    characterizing each of the particle of the first cluster of particles as a sphere;
    determining the refractive index and the radius for characterized sphere of the first cluster of particles
    generating a second set of holograms based upon holographic video microscopy of a second cluster of particles within the observation volume at a second time;
    characterizing each of the particles of the second cluster of particle as a sphere; and
    determining the refractive index and the radius for each of the particles of the second cluster of particles by characterizing of each of the particles of the first cluster and each of the particles of the second cluster as a fractal cluster of fractal dimension D where:

$$\ln\left(\frac{f(n_p) - f(n_m)}{f(n_0) - f(n_m)}\right) = (3 - D)\ln\left(\frac{a_0}{a_p}\right)$$

with Ø being a volume fraction of particle, $a_0$ being the particle radius, and $a_p$ being the particles radius, $n_0$ being a refractive index of a particle, $n_m$ being a refractive index of the medium, and $n_p$ being an apparent refractive index of the respective particle cluster.

2. The method of claim 1, further comprising monitoring synthesis of the plurality of particles based upon comparison of the first particle refractive index and radius and the second particle refractive index and radius.

3. The method of claim 1, further comprising, wherein flowing the sample is at a rate of up to 100 μm s$^{-1}$.

4. The method of claim 1, further comprising prior to generating the first set of holograms, adding salt.

5. The method of claim 1, wherein determining the refractive index and the radius comprises application of Lorenz-Mie theory.

6. The method of claim 2, further comprising determining whether synthesis of the plurality of particles has concluded.

7. The method of claim 1, wherein determining the refractive index and the radius of the particles of the first cluster of particles and determining the refractive index and the radius of the particles of the second cluster of particles comprise determining a probability density for refractive index and radius of the particles of the first cluster of particles and determining a probability density for refractive index and radius of the particles of the second cluster of particles, respectively.

8. The method of claim 1, wherein at least one protein aggregate is present in both the first cluster of particles and the second cluster of particles and further wherein the trajectory of the at least one particle is determined.

9. A computer-implemented machine for characterizing a plurality of particles, comprising:
    a processor;
    a holographic microscope comprising a coherent light, a specimen stage having an observation volume, an objective lens, and an image collection device, the holographic microscope in communication with the processor; and
    a tangible computer-readable medium operatively connected to the processor and including computer code configured to:
        flow the sample in a medium through an observation volume of a holographic microscope;
        generate a first of holograms based upon holographic video microscopy of a particle $P_n$ of a first cluster of the plurality of particles within the observation volume at a first time;
        characterize each of the particles of the first cluster of the plurality of particles as a sphere;
        determine the refractive index and the radius for characterized sphere of the first cluster of particles generate a second of holograms based upon holographic video microscopy of a second cluster of the plurality particles within the observation volume at a second time;

characterize each of the particles of the second cluster of particle as a sphere; and determine the refractive index and the radius for each of the particles of the second cluster by the characterizing of each of the particles of the first cluster and of the second cluster as a fractal cluster of fractal dimension D where:

$$\ln\left(\frac{f(n_p) - f(n_m)}{f(n_0) - f(n_m)}\right) = (3-D)\ln\left(\frac{a_0}{a_p}\right)$$

with Ø being a volume fraction of particle, $a_0$ being particle radius, $a_p$ being particle cluster radius; $n_0$ being a refractive index of a particle, $n_m$ being a refractive index of the medium, and $n_p$ being an apparent refractive index of the respective particle cluster.

10. The computer-implemented machine of claim 9, further wherein the tangible computer readable medium includes computer code to monitor synthesis of the plurality of particles based upon comparison of the first particle refractive index and radius and the second particle refractive index and radius.

11. The computer-implemented machine of claim 10, further wherein the tangible computer readable medium includes computer code to determine whether synthesis of the plurality of particles has concluded.

12. The computer-implemented machine of claim 9, further comprising, wherein flowing the sample is at a rate of up to 100 μm s$^{-1}$.

13. The computer-implemented machine of claim 9, further wherein the tangible computer readable medium includes computer code to, prior to generating the first of holograms, add salt.

14. The computer-implemented machine of claim 9, wherein determining the refractive index and the radius comprises application of Lorenz-Mie theory.

* * * * *